(12) United States Patent
Takano et al.

(10) Patent No.: US 10,464,916 B2
(45) Date of Patent: Nov. 5, 2019

(54) FLUORINATED UNSATURATED CYCLIC CARBONATE AND PROCESS FOR PRODUCING THE SAME

(71) Applicant: DAIKIN INDUSTRIES, LTD., Osaka-Shi, Osaka (JP)

(72) Inventors: Shinya Takano, Osaka (JP); Mayuko Takano, Osaka (JP); Akinori Tani, Osaka (JP); Michiaki Okada, Osaka (JP); Hideo Sakata, Osaka (JP); Tomo Shimada, Osaka (JP); Shinichi Kinoshita, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/285,016

(22) Filed: Feb. 25, 2019

(65) Prior Publication Data
US 2019/0185445 A1   Jun. 20, 2019

Related U.S. Application Data

(63) Continuation of application No. 15/528,017, filed as application No. PCT/JP2015/082542 on Nov. 19, 2015, now Pat. No. 10,287,263.

(30) Foreign Application Priority Data

Nov. 21, 2014  (JP) .................. 2014-236700

(51) Int. Cl.
C07D 317/40 (2006.01)
H01G 11/64 (2013.01)
H01M 10/0567 (2010.01)
H01M 10/0525 (2010.01)

(52) U.S. Cl.
CPC .......... *C07D 317/40* (2013.01); *H01G 11/64* (2013.01); *H01M 10/0525* (2013.01); *H01M 10/0567* (2013.01); *H01M 2300/0025* (2013.01); *Y02E 60/13* (2013.01)

(58) Field of Classification Search
CPC .......... C07D 317/40; H01M 10/0525; H01M 10/0567; H01M 2300/0025; H01G 11/64; Y02E 60/13
See application file for complete search history.

(56) References Cited

U.S. PATENT DOCUMENTS

| | | | |
|---|---|---|---|
| 2006/0154149 A1 | 7/2006 | Arai et al. | |
| 2007/0275306 A1 | 11/2007 | Lee et al. | |
| 2008/0254361 A1 | 10/2008 | Horikawa | |
| 2009/0082586 A1 | 3/2009 | Lerm et al. | |
| 2015/0004484 A1 | 1/2015 | Nishizawa et al. | |

FOREIGN PATENT DOCUMENTS

| | | |
|---|---|---|
| EP | 2 045 249 A1 | 4/2009 |
| EP | 2 216 844 A2 | 8/2010 |
| JP | 11-307120 A | 11/1999 |
| JP | 2001-035530 A | 2/2001 |
| JP | 2001-338680 A | 12/2001 |
| JP | 2003-132946 A | 5/2003 |
| JP | 2003-257479 A | 9/2003 |
| JP | 2004-087168 A | 3/2004 |
| JP | 2006-164860 A | 6/2006 |
| JP | 2006-179458 A | 7/2006 |
| JP | 2006-286570 A | 10/2006 |
| JP | 2006-294414 A | 10/2006 |
| JP | 2007-317647 A | 12/2007 |
| JP | 2009-073837 A | 4/2009 |
| JP | 2009-238765 A | 10/2009 |
| JP | 2010-238505 A | 10/2010 |
| JP | 2011-100750 A | 5/2011 |
| JP | 2012-38737 A | 2/2012 |
| JP | 2012-43628 A | 3/2012 |
| JP | 2012-162516 A | 8/2012 |
| WO | 2012/067248 A1 | 5/2012 |
| WO | 2013/094603 A1 | 6/2013 |

OTHER PUBLICATIONS

International Search Report for PCT/JP2015/082542 dated Jan. 26, 2016 [PCT/ISA/210].

International Preliminary Report on Patentability and Translation of Written Opinion dated May 23, 2017, from the International Bureau in counterpart International application No. PCT/JP2015/082542.

Hashimoto, T. S., et al. "Development of lithium ion battery and grid stabilization technology for renewable energy using secondary battery system." Mitsubishi Heavy Industries Technical Review 44.4 (2007): 27-31.

Communication dated Jul. 3, 2019 by the European Patent Office in application No. 15861588.0.

*Primary Examiner* — John M Mauro
(74) *Attorney, Agent, or Firm* — Sughrue Mion, PLLC

(57) ABSTRACT

An electrolyte solution containing a compound represented by the following formula (1):

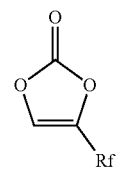

wherein Rf is a C1-C8 fluorinated alkyl group, and vinylene carbonate. Also disclosed is an electrochemical device including the electrolyte solution, a lithium ion secondary battery including the electrolyte solution and a module including the lithium ion secondary battery.

4 Claims, No Drawings

FLUORINATED UNSATURATED CYCLIC CARBONATE AND PROCESS FOR PRODUCING THE SAME

CROSS-REFERENCE TO RELATED APPLICATIONS

This is a Rule 53(b) Continuation Application of application Ser. No. 15/528,017 filed May 18, 2017, which is a National Stage of International Application No. PCT/JP2015/082542, filed Nov. 19, 2015, which claims priority from Japanese Patent Application No. 2014-236700 filed Nov. 21, 2014, the contents of all of which are incorporated herein by reference in their entirety.

TECHNICAL FIELD

The present invention relates to a novel fluorinated unsaturated cyclic carbonate and a process for producing the same.

BACKGROUND ART

Patent Literature 1 discloses a vinylene carbonate represented by the following formula (1).

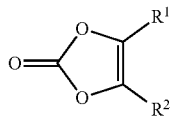
(1)

In the formula (1), $R^1$ and $R^2$ may be the same as or different from each other, and are each a hydrogen atom, a halogen atom, or a C1-C12 alkyl group which may optionally contain a halogen atom.

Patent Literature 2 discloses the following formula.

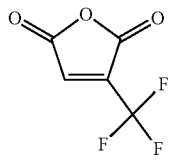 [SMILES: O=C1C=C(C(F)(F)F)C(=O)O1]

Patent Literature 3 discloses a compound represented by the following (Formula 4):

[Chem. 3]

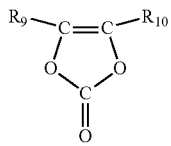
(Formula 4)

wherein $R_9$ and $R_{10}$ are each hydrogen, fluorine, chlorine, a C1-C3 alkyl group, or a fluorinated alkyl group, and $R_9$ and $R_{10}$ may be the same as or different from each other.

Patent Literature documents 4 to 7 also disclose unsaturated cyclic carbonates.

Although each of these documents specifically discloses the use of an electrolyte solution containing vinylene carbonate or a fluorinated carbonate, they disclose neither actual use of an unsaturated cyclic carbonate containing a fluorinated alkyl group nor any method for synthesizing or acquiring the same.

CITATION LIST

Patent Literature

Patent Literature 1: JP 2003-257479 A
Patent Literature 2: JP 2007-317647 A
Patent Literature 3: JP 2006-164860 A
Patent Literature 4: JP 2006-294414 A
Patent Literature 5: JP 2011-100750 A
Patent Literature 6: JP 2006-286570 A
Patent Literature 7: JP 2006-179458 A

SUMMARY OF INVENTION

Technical Problem

As mentioned above, an unsaturated cyclic carbonate containing a fluorinated alkyl group and the usefulness thereof have never been known before the filing date of this application.

In consideration of the above state of the art, the present invention aims to provide an unsaturated cyclic carbonate containing a fluorinated alkyl group and a process for producing the same.

Solution to Problem

The present invention relates to a compound represented by the following formula (1):

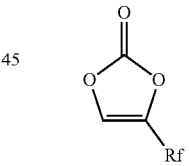

wherein Rf is a C1-C8 fluorinated alkyl group.

In the formula (1), Rf is preferably a C2-C8 fluorinated alkyl group.

The present invention also relates to an electrolyte solution containing the above compound.

The present invention also relates to an electrochemical device containing the above electrolyte solution.

The present invention also relates to a lithium ion secondary battery containing the above electrolyte solution.

The present invention also relates to a module including the above lithium ion secondary battery.

The present invention also relates to a production process including reacting a compound (2-1) represented by the following formula (2-1):

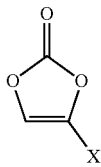

wherein X is a halogen atom, with a fluoroalkylating agent to provide a compound represented by the following formula (1):

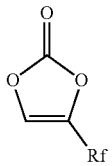

wherein Rf is a C1-C8 fluorinated alkyl group.

The present invention also relates to a production process including
reacting a compound (3-1) represented by the following formula (3-1):

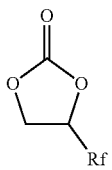

wherein Rf is a C1-C8 fluorinated alkyl group, with a halogenating agent to provide a compound (3-2) represented by the following formula (3-2):

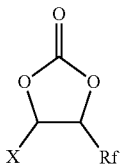

wherein Rf is defined in the same manner as mentioned above; and X is a halogen atom, and
reacting the compound (3-2) with a base or metal to provide a compound represented by the following formula (1):

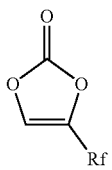

wherein Rf is defined in the same manner as mentioned above.

The present invention also relates to a production process including
reacting a compound (4-1) represented by the following formula (4-1):

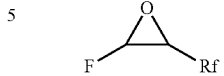

wherein Rf is a C1-C8 fluorinated alkyl group, with carbon dioxide to provide a compound (4-2) represented by the following formula (4-2):

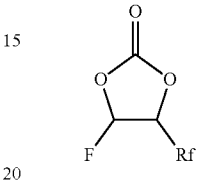

wherein Rf is defined in the same manner as mentioned above, and
reacting the compound (4-2) with a base or metal to provide a compound represented by the following formula (1):

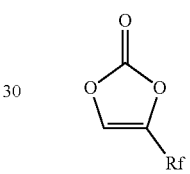

wherein Rf is defined in the same manner as mentioned above.

The present invention also relates to a production process including reacting vinylene carbonate with a compound (5-1) represented by the following formula (5-1):

Rf—X wherein Rf is a C1-C8 fluorinated alkyl group; and X is a halogen atom, to provide a compound (5-2) represented by the following formula (5-2):

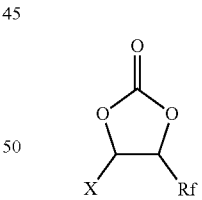

wherein Rf is defined in the same manner as mentioned above; and X is a halogen atom, and
reacting the compound (5-2) with a base or metal to provide a compound represented by the following formula (1):

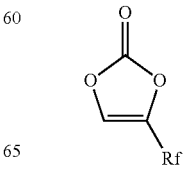

wherein Rf is defined in the same manner as mentioned above.

Advantageous Effects of Invention

The present invention can provide an unsaturated cyclic carbonate containing a fluorinated alkyl group. This novel unsaturated cyclic carbonate is useful as a component constituting an electrolyte solution to be used in an electrochemical device such as a lithium ion secondary battery.

DESCRIPTION OF EMBODIMENTS

The present invention will be specifically described hereinbelow.

The novel compound of the present invention is a fluorinated unsaturated cyclic carbonate represented by the following formula (1):

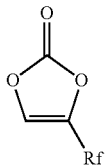

wherein Rf is a C1-C8 fluorinated alkyl group.

In the formula (1), Rf may be either a perfluorinated alkyl group or a partially fluorinated alkyl group, and is preferably a perfluorinated alkyl group. Rf may contain an ether bond.

In the formula (1), the fluorinated alkyl group may be either linear or branched.

In the formula (1), Rf has a carbon number of 8 or less, preferably 6 or less. Rf may have a carbon number of 2 or more.

In the formula (1), Rf is preferably at least one selected from the group consisting of $CF_3-$, $CF_3CF_2-$, $CF_3CF_2CF_2-$, $CF_3CF_2CF_2CF_2-$, $CF_3CF_2CF_2CF_2CF_2-$, $CF_3CF_2CF_2CF_2CF_2CF_2-$, $CF_3CF_2CF_2CF_2CF_2CF_2CF_2-$, $CF_3CF_2CF_2CF_2CF_2CF_2CF_2CF_2-$, $(CF_3)_2CF-$, $CF_3CH_2-$, $CF_3CF_2CH_2-$, $CF_3CF_2CF_2CH_2-$, $CF_3CF_2CF_2CF_2CH_2-$, $CF_3CF_2CF_2CF_2CF_2CH_2-$, $CF_3CF_2CF_2CF_2CF_2CF_2CH_2-$, $CF_3CF_2CF_2CF_2CF_2CF_2CF_2CH_2-$, $CF_3CF_2CF_2CF_2CF_2CF_2CF_2CF_2CH_2-$, and $(CF_3)_2CFCH_2-$, more preferably at least one selected from the group consisting of $CF_3-$, $CF_3CF_2-$, $CF_3CF_2CF_2-$, $CF_3CF_2CF_2CF_2-$, $CF_3CF_2CF_2CF_2CF_2CF_2-$, and $(CF_3)_2CF-$.

The above novel compound can suitably be produced by any of the following four methods.

A first production process includes reacting a compound (2-1) represented by the following formula (2-1):

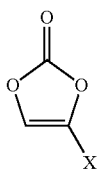

(wherein X is a halogen atom) with a fluoroalkylating agent to provide a compound represented by the following formula (1):

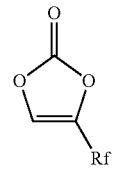

(wherein Rf is a C1-C8 fluorinated alkyl group).

In other words, the first production process provides the target fluorinated unsaturated cyclic carbonate by fluoroalkylation of a known halogenated unsaturated cyclic carbonate.

X in the formula (2-1) is a halogen atom, and is preferably a fluorine atom, a chlorine atom, a bromine atom, or an iodine atom, more preferably a chlorine atom, a bromine atom, or an iodine atom, particularly preferably a bromine atom or an iodine atom.

The first production process is classified into three processes, i.e., Process (1-1) of using a telomer as a fluoroalkylating agent, Process (1-2) of using a mercury compound as a fluoroalkylating agent, and Process (1-3) of using a silicon compound as a fluoroalkylating agent.

In Process (1-1), preferred examples of a compound to be used as the fluoroalkylating agent include compounds represented by RfI (Rf is a C1-C8 fluorinated alkyl group) and compounds represented by RfBr (Rf is defined in the same manner as mentioned above). More preferred examples thereof include perfluoroalkyl iodides and perfluoroalkyl bromides.

In Process (1-1), the reaction between the compound (2-1) and the fluoroalkylating agent is preferably performed in an organic solvent. Preferred examples of the organic solvent include diethyl ether, diisopropyl ether, ethyl methyl ether, cyclopentyl methyl ether, methyl-t-butyl ether, and tetrahydrofuran. More preferred examples thereof include cyclopentyl methyl ether, methyl-t-butyl ether, and tetrahydrofuran. Particularly preferred are cyclopentyl methyl ether and tetrahydrofuran.

In Process (1-1), the reaction between the compound (2-1) and the fluoroalkylating agent is preferably performed in the presence of zinc and a transition metal catalyst. Preferred examples of the transition metal catalyst include palladium chloride, palladium acetate, bistriphenylphosphinepalladium dichloride, bis(p-cyanophenyl)palladium dichloride, tetrakistriphenylphosphinepalladium, bisacetylacetonatopalladium, and bisdibenzylideneacetonepalladium. More preferred are palladium acetate, bistriphenylphosphinepalladium dichloride, and tetrakistriphenylphosphinepalladium.

In Process (1-1), the reaction between the compound (2-1) and the fluoroalkylating agent may be performed under ultrasonic irradiation.

In Process (1-1), the reaction can be quenched by adding an aqueous solution such as an aqueous solution of sodium chloride. Addition of the aqueous solution to the reaction solution causes separation of the solution into two layers. A solution containing the compound (1) can be then obtained by collecting an organic layer by liquid separation.

It is acceptable to add a desiccant such as magnesium sulfate, a hydrate of sodium sulfate (mirabilite), or molecular sieve to the resulting solution containing the compound (1), to filter out the desiccant and collect the solution containing the compound (1) as a filtrate, and then to concentrate the solution.

The compound (1) can be highly purified by distilling the resulting solution containing the compound (1) or sublimating the compound (1) from the solution. The purification technique is not limited to distillation or sublimation. If desired, the purification can be achieved by any known purification technique such as solvent extraction, drying, filtering, distillation, concentration, column chromatography, recrystallization, and any combination thereof.

In Process (1-2), preferred examples of a compound to be used as the fluoroalkylating agent include compounds represented by $Rf_2Hg$ (Rf is a C1-C8 fluorinated alkyl group). More preferred examples thereof include $(CF_3)_2Hg$, $(C_2F_5)_2Hg$, and $(C_6F_{13})_2Hg$.

In Process (1-2), the reaction between the compound (2-1) and the fluoroalkylating agent is preferably performed in an organic solvent. Preferred examples of the organic solvent include N-methylpyrrolidone, dimethylformamide, dimethylacetamide, acetone, methyl acetate, ethyl acetate, diethyl ether, diisopropyl ether, tetrahydrofuran, glyme, tetraglyme, and sulfolane. More preferred examples thereof include N-methylpyrrolidone, dimethylformamide, dimethylacetamide, acetone, methyl acetate, ethyl acetate, diethyl ether, glyme, tetraglyme, and sulfolane. Particularly preferred are N-methylpyrrolidone, dimethylformamide, dimethylacetamide, and sulfolane.

In Process (1-2), the reaction between the compound (2-1) and the fluoroalkylating agent is preferably performed in the presence of a simple metal or a metal salt. Preferred examples of the simple metal include zinc and copper. More preferred is copper. Preferred examples of the metal salt include copper fluoride, copper chloride, copper bromide, and copper iodide. More preferred are copper bromide and copper iodide. The reaction can be performed in the presence of both a simple metal and a metal salt.

In Process (1-2), the reaction can be quenched by adding an aqueous solution such as an aqueous solution of sodium chloride. Addition of the aqueous solution to the reaction solution causes separation of the solution into two layers. A solution containing the compound (1) can be then obtained by collecting an organic layer by liquid separation.

In Process (1-2), a water-insoluble organic solvent may be added to the reaction solution before the liquid separation so as to improve the liquid-separating performance. Examples of the water-insoluble organic solvent include diethyl ether, diisopropyl ether, and ethyl acetate.

It is acceptable to add a desiccant such as magnesium sulfate, a hydrate of sodium sulfate (mirabilite), or molecular sieve to the resulting solution containing the compound (1), to filter out the desiccant and collect the solution containing the compound (1) as a filtrate, and then to concentrate the solution.

The compound (1) can be highly purified by distilling the resulting solution containing the compound (1) or sublimating the compound (1) from the solution. The purification technique is not limited to distillation or sublimation. If desired, the purification can be achieved by any known purification technique such as solvent extraction, drying, filtering, distillation, concentration, column chromatography, recrystallization, and any combination thereof.

In Process (1-3), preferred examples of a compound to be used as the fluoroalkylating agent include compounds represented by RfTMS (Rf is a C1-C8 fluorinated alkyl group; and TMS is a trimethylsilyl group) and compounds represented by RfTES (Rf is defined in the same manner as mentioned above; and TES is a triethylsilyl group). More preferred examples thereof include $CF_3TMS$, $C_2F_5TMS$, $C_4F_9TMS$, $C_6F_{13}TMS$, $CF_3TES$, $C_2F_5TES$, $C_4F_9TES$, and $C_6F_{13}TES$.

In Process (1-3), the reaction between the compound (2-1) and the fluoroalkylating agent is preferably performed in an organic solvent. Preferred examples of the organic solvent include N-methylpyrrolidone, dimethylformamide, dimethylacetamide, dimethylpropyleneurea, glyme, tetraglyme, and sulfolane. More preferred examples thereof include N-methylpyrrolidone, dimethylformamide, dimethylacetamide, and dimethylpropyleneurea. Particularly preferred are N-methylpyrrolidone, dimethylformamide, and dimethylpropyleneurea.

In Process (1-3), the reaction between the compound (2-1) and the fluoroalkylating agent is preferably performed in the presence of a copper salt and a metal fluoride. Preferred examples of the copper salt include copper fluoride, copper chloride, copper bromide, copper iodide, and copper acetate. More preferred are copper chloride and copper iodide. Preferred examples of the metal fluoride include lithium fluoride, sodium fluoride, and potassium fluoride. More preferred is potassium fluoride.

In Process (1-3), the reaction between the compound (2-1) and the fluoroalkylating agent may be performed in the presence of a ligand. Preferred examples of the ligand include 1,10-phenanthroline, tetramethylethylenediamine, and 2,2'-bipyridine. Particularly preferred are 1,10-phenanthroline and 2,2'-bipyridine.

In Process (1-3), the reaction can be quenched by adding an aqueous solution such as an aqueous solution of sodium chloride. Addition of the aqueous solution to the reaction solution causes separation of the solution into two layers. A solution containing the compound (1) can be then obtained by collecting an organic layer by liquid separation.

In Process (1-3), a water-insoluble organic solvent may be added to the reaction solution before the liquid separation so as to improve the liquid-separating performance. Examples of the water-insoluble organic solvent include diethyl ether, diisopropyl ether, and ethyl acetate.

It is acceptable to add a desiccant such as magnesium sulfate, a hydrate of sodium sulfate (mirabilite), or molecular sieve to the resulting solution containing the compound (1), to filter out the desiccant and collect the solution containing the compound (1) as a filtrate, and then to concentrate the solution.

The compound (1) can be highly purified by distilling the resulting solution containing the compound (1) or sublimating the compound (1) from the solution. The purification technique is not limited to distillation or sublimation. If desired, the purification can be achieved by any known purification technique such as solvent extraction, drying, filtering, distillation, concentration, column chromatography, recrystallization, and any combination thereof.

A second production process includes reacting a compound (3-1) represented by the following formula (3-1):

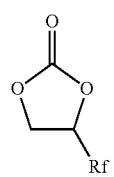

(wherein Rf is a C1-C8 fluorinated alkyl group) with a halogenating agent to provide a compound (3-2) represented by the following formula (3-2):

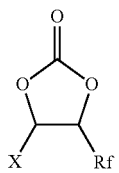

(wherein Rf is defined in the same manner as mentioned above; and X is a halogen atom), and reacting the compound (3-2) with a base to provide a compound represented by the following formula (1):

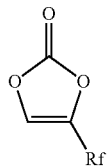

(wherein Rf is defined in the same manner as mentioned above).

In other words, the second production process provides the target fluorinated unsaturated cyclic carbonate by halogenation of a known fluorinated saturated cyclic carbonate and the following dehydrohalogenation of the resulting compound. The fluorinated saturated cyclic carbonate obtained by the halogenation needs not to be isolated, and can be subjected to the dehydrohalogenation as it is.

Rf in each of the formula (3-1) and the formula (3-2) is defined in the same manner as Rf in the aforementioned formula (1).

X in the formula (3-2) is a halogen atom, and is preferably a chlorine atom, a bromine atom, or an iodine atom.

The halogenating agent to be used may be a single halogen such as fluorine ($F_2$), chlorine ($Cl_2$), bromine ($Br_2$), or iodine ($I_2$), or a halogenating reagent. Preferred among these is fluorine ($F_2$), chlorine ($Cl_2$), bromine ($Br_2$), or a halogenating reagent.

The reaction between the compound (3-1) and the simple halogen can be performed in a solvent, preferably in an organic solvent such as a halogen-containing solvent. If fluorine is used as a halogen, the organic solvent is preferably a fluorine-containing solvent. If chlorine, bromine, or iodine is used, the reaction is preferably performed in carbon tetrachloride or a like organic solvent.

Also in the case of using a halogenating reagent, the above reaction can be performed in an organic solvent. The organic solvent in this case may be any organic solvent that does not react with a base to be used in the next step.

The halogenating reagent may be any of those containing a fluorine atom (fluorinating agents), those containing a chlorine atom (chlorinating agents), those containing a bromine atom (brominating agents), and those containing an iodine atom (iodizing agents).

Examples of the fluorinating agents include 1-fluoropyridinium tetrafluoroborate, 1-fluoropyridinium triflate, 1-fluoro-2,4,6-trimethylpyridinium tetrafluoroborate, 1-fluoro-2,4,6-trifluoromethylpyridinium trifluoromethanesulfonate, N-fluoro-N'-(chloromethyl)-triethylenediaminebis(tetrafluoroborate), N-fluorobenzenesulfonimide, tetrabutylammonium difluorotriphenyltin, 2,6-dichloro-1-fluoropyridinium trifluoromethanesulfonate, and 1,1'-difluoro-2,2'-bipyridinium bis(tetrafluoroborate). Preferred is N-fluoro-N'-(chloromethyl)-triethylenediaminebis(tetrafluoroborate) or N-fluorobenzenesulfonimide.

Examples of the chlorinating agents include tert-butyl hypochlorite, N-chlorophthalimide, N-chlorosuccinimide, cyanuric chloride, oxalyl chloride, sodium dichloroisocyanurate, trichloroisocyanuric acid, trichloromethane, and thionyl chloride. Preferred is N-chlorophthalimide, N-chlorosuccinimide, oxalyl chloride, trichloromethane, or thionyl chloride.

Examples of the brominating agents include boron tribromide, N-bromoacetamide, bromodimethyl bromide, N-bromophthalimide, N-bromosaccharin, N-bromosuccinimide, 1-butyl-3-methylimidazolium tribromide, 1,3-dibromo-5,5-dimethylhydantoin, dibromoisocyanuric acid, 5,5-dibromomeldrum's acid, 4-dimethylaminopyridinium bromide perbromide, pyridinium bromide perbromide, 2,4,4,6-tetrabromo-2,5-cyclohexadienone, tetrabutylammonium tribromide, trimethylphenylammonium bromide, and triphenylphosphine dibromide. Preferred is boron tribromide, N-bromophthalimide, N-bromosuccinimide, 1,3-dibromo-5,5-dimethylhydantoin, dibromoisocyanuric acid, or 5,5-dibromomeldrum's acid.

Examples of the iodizing agents include 1,3-diiodo-5,5-dimethylhydantoin, N-iodosaccharin, and N-iodosuccinimide.

The reaction between the compound (3-1) and the simple halogen can be progressed by applying heat or light. The light is preferably ultraviolet rays.

Then, the reaction can be quenched by adding a reducing agent. The reducing agent may be added in the form of an aqueous solution. When the reaction between the compound (3-1) and the halogenating agent is performed in a water-insoluble organic solvent, addition of the reducing agent in the form of an aqueous solution to the reaction product causes separation of the solution into two layers. A solution containing the compound (3-2) can be then obtained by collecting an organic layer by liquid separation.

Next, the compound (3-2) is reacted with a base or metal. This reaction can be performed in the solvent used in the reaction for providing the compound (3-2). Alternatively, it is acceptable to distill the solvent from the solution containing the compound (3-2) and to add a solvent that is different from the solvent used in the reaction for providing the compound (3-2), and then to react the compound (3-2) with a base or metal in this solvent.

The base may be either an organic base or an inorganic base. Preferred among these are triethylamine, diisopropylethylamine, and tert-butoxypotassium.

The metal is preferably zinc.

The base or metal may be added to the solution containing the compound (3-2) which is collected after the reaction is quenched by adding the reducing agent. Alternatively, the reducing agent and the base or metal may be added at the same time to a solution obtained by reacting the compound (3-1) and the halogenating agent. In this case, the two steps can be successively performed in the same container.

Then, the reaction can be quenched by adding an acidic aqueous solution. When the reaction between the compound (3-2) and the base or metal is performed in a water-insoluble organic solvent, addition of the acidic aqueous solution to the reaction product causes separation of the solution into two layers. A solution containing the compound (1) can be then obtained by collecting an organic layer by liquid separation.

It is acceptable to add a desiccant such as magnesium sulfate, a hydrate of sodium sulfate (mirabilite), or molecular sieve to the resulting solution containing the compound (1), to filter out the desiccant and collect the solution containing the compound (1) as a filtrate, and then to concentrate the solution.

The compound (1) can be highly purified by distilling the resulting solution containing the compound (1) or sublimating the compound (1) from the solution. The purification technique is not limited to distillation or sublimation. If desired, the purification can be achieved by any known purification technique such as solvent extraction, drying, filtering, distillation, concentration, column chromatography, recrystallization, and any combination thereof.

A third production process includes reacting a compound (4-1) represented by the following formula (4-1):

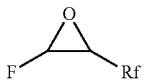

(wherein Rf is a C1-C8 fluorinated alkyl group) with carbon dioxide to provide a compound (4-2) represented by the following formula (4-2):

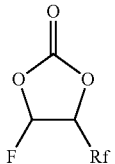

(wherein Rf is defined in the same manner as mentioned above), and reacting the compound (4-2) with a base to provide a compound represented by the following formula (1):

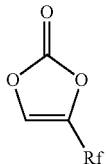

(wherein Rf is defined in the same manner as mentioned above).

In other words, the third production process provides the target fluorinated unsaturated cyclic carbonate by allowing carbon dioxide to act on a known fluorinated epoxy compound to provide a fluorinated saturated cyclic carbonate and the following dehydrohalogenation of the resulting fluorinated saturated cyclic carbonate. The fluorinated saturated cyclic carbonate obtained needs not to be isolated, and can be directly subjected to the dehydrohalogenation.

Rf in each of the formula (4-1) and the formula (4-2) is defined in the same manner as Rf in the aforementioned formula (1).

The reaction between the compound (4-1) and carbon dioxide can be performed in a solvent, and the solvent may be either an organic solvent or water. Preferred examples of the organic solvent include N-methylpyrrolidone, dimethylformamide, acetone, methyl acetate, ethyl acetate, diethyl ether, diisopropyl ether, tetrahydrofuran, glyme, tetraglyme, and sulfolane. More preferred examples thereof include N-methylpyrrolidone, dimethylformamide, acetone, methyl acetate, ethyl acetate, diethyl ether, glyme, tetraglyme, and sulfolane. Particularly preferred are N-methylpyrrolidone, dimethylformamide, acetone, and sulfolane.

The reaction between the compound (4-1) and carbon dioxide is preferably performed in the presence of a salt. The salt is preferably at least one selected from the group consisting of NaF, NaCl, NaBr, NaI, LiF, LiCl, LiBr, LiI, KF, KCl, KBr, and KI, more preferably at least one selected from the group consisting of LiF, LiCl, LiBr, and LiI.

The reaction between the compound (4-1) and carbon dioxide can be performed at 0° C. to 100° C., preferably 15° C. to 80° C.

In the case of using an organic solvent in the reaction, the reaction can be quenched by adding, for example, water.

In the case of using water as a solvent in the reaction, the quenching may be replaced by extraction using an organic solvent.

When the reaction between the compound (4-1) and carbon dioxide is performed in a water-soluble organic solvent and the reaction is quenched by adding water, addition of a water-insoluble organic solvent to the reaction product causes separation of the solution into two layers. A solution containing the compound (4-2) can be then obtained by collecting an organic layer by liquid separation. Examples of the water-insoluble organic solvent include diethyl ether, diisopropyl ether, and ethyl acetate.

It is acceptable to add a desiccant such as magnesium sulfate, a hydrate of sodium sulfate (mirabilite), or molecular sieve to the solution containing the compound (4-2), and to filter out the desiccant and collect the solution containing the compound (4-2) as a filtrate. This solution may be subjected to the next step.

Next, the compound (4-2) is reacted with a base or metal.

This reaction can be performed in the solvent used in the reaction for providing the compound (4-2). Alternatively, it is acceptable to distill the solvent from the solution containing the compound (4-2) and to add a solvent that is different from the solvent used in the reaction for providing the compound (4-2), and then to react the compound (4-2) with a base or metal in this solvent.

The base may be either an organic base or an inorganic base. Preferred among these are triethylamine, diisopropylethylamine, and tert-butoxypotassium.

The metal is preferably zinc.

The base or metal may be added to the solution containing the compound (4-2) which is collected after the reaction is quenched by adding water or any appropriate substance. Alternatively, water or any appropriate substance and the base or metal may be added at the same time to a solution obtained by reacting the compound (4-1) and the halogenating agent. In this case, the two steps can be successively performed in the same container.

Then, the reaction can be quenched by adding an acidic aqueous solution. When the reaction between the compound (4-2) and the base or metal is performed in a water-insoluble organic solvent, addition of the acidic aqueous solution to the reaction product causes separation of the solution into two layers. A solution containing the compound (1) is then obtained by collecting an organic layer by liquid separation.

It is acceptable to add a desiccant such as magnesium sulfate, a hydrate of sodium sulfate (mirabilite), or molecular sieve to the resulting solution containing the compound (1), to filter out the desiccant and collect the solution containing the compound (1) as a filtrate, and then to concentrate the solution.

The compound (1) can be highly purified by distilling the resulting solution containing the compound (1) or sublimating the compound (1) from the solution. The purification technique is not limited to distillation or sublimation. If desired, the purification can be achieved by any known purification technique such as solvent extraction, drying, filtering, distillation, concentration, column chromatography, recrystallization, and any combination thereof.

A fourth production process includes reacting vinylene carbonate with a compound (5-1) represented by the following formula (5-1):

(wherein Rf is a C1-C8 fluorinated alkyl group; and X is a halogen atom) to provide a compound (5-2) represented by the following formula (5-2):

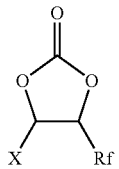

(wherein Rf is defined in the same manner as mentioned above; and X is a halogen atom), and reacting the compound (5-2) with a base or metal to provide a compound represented by the following formula (1):

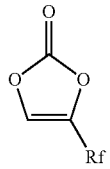

(wherein Rf is defined in the same manner as mentioned above).

In other words, the fourth production process provides the target fluorinated unsaturated cyclic carbonate by allowing a fluorinated alkyl halide to act on a known vinylene carbonate to provide a fluorinated saturated cyclic carbonate and the following dehydrohalogenation of the resulting fluorinated saturated cyclic carbonate. The fluorinated saturated cyclic carbonate obtained needs not to be isolated, and can be directly subjected to the dehydrohalogenation.

Rf in each of the formula (5-1) and the formula (5-2) is defined in the same manner as Rf in the aforementioned formula (1).

X in each of the formula (5-1) and the formula (5-2) is a halogen atom, and is preferably a chlorine atom, a bromine atom, or an iodine atom, particularly preferably an iodine atom.

The reaction between the vinylene carbonate and the compound (5-1) may be performed without a solvent or in a solvent. In the case of using a solvent in the reaction, the solvent may be either an organic solvent or water. Preferred examples of the organic solvent include diethyl ether, tetrahydrofuran, ethylene glycol, hexane, benzene, toluene, benzotrifluoride, dimethylformamide, and dichloromethane. More preferred examples thereof include benzene, toluene, benzotrifluoride, dimethylformamide, and dichloromethane. Still more preferred are toluene, benzotrifluoride, and dichloromethane.

The reaction between the vinylene carbonate and the compound (5-1) can be progressed by adding a radical initiator or by applying heat without a radical initiator.

The radical initiator may be an organic radical initiator or may be an inorganic radical initiator.

The organic radical initiator is preferably an azo compound, an organic peroxide, or an organic metal compound. Preferred examples of the azo compound include 2,2'-azobis (isobutyronitrile), 1,1'-azobis(cyclohexane-1-carbonitrile), 1-[(1-cyano-1-methylethyl)azo]formamide, 4,4'-azobis(4-cyanovaleric acid), dimethyl-1,1'-azobis(1-cyclohexanecarboxylate), 2,2'-azobis(N-butyl-2-methylpropionamide), and 2,2'-azobis(N-cyclohexyl-2-methylpropionamide). Preferred examples of the organic peroxide include dibenzoyl peroxide, di-(3-methylbenzoyl)peroxide, benzoyl(3-methylbenzoyl)peroxide, 1,1-di(t-hexylperoxy)-3,3,5-trimethylcyclohexane, 1,1-di(t-hexylperoxy)cyclohexane, 1,1-di(t-butylperoxy)-2-methylcyclohexane, 1,1-di(t-butylperoxy) cyclohexane, 2,2-di(t-butylperoxy)butane, t-butylcumyl peroxide, di-t-hexyl peroxide, di-t-butyl peroxide, 1,1,3,3-tetramethylbutylperoxy-2-ethylhexanoate, t-hexylperoxy-2-ethylhexanoate, t-butylperoxy-2-ethylhexanoate, t-hexylperoxyisopropylmonocarbonate, t-butylperoxyisopropylmonocarbonate, t-butylperoxy-2-ethylhexylmonocarbonate, and 2,5-dimethyl-2,5-di(benzoylperoxy)hexane. Preferred examples of the organic metal compound include triethylborane, diethylzinc, and trimethylaluminum.

The inorganic radical initiator may be a simple metal, a metal salt, or a like substance. Preferred examples of the simple metal include zinc, copper, and silver. The reaction may be performed in the presence of multiple simple metals. Examples of the metal salt include $Na_2S_2O_3$, $Na_2S_2O_4$, CuF, CuCl, CuBr, CuI, $FeCl_2$, $FeBr_2$, $FeSO_4$, Fe $(acac)_2$, AgF, AgCl, AgBr, and AgI. More preferred are $Na_2S_2O_3$, $Na_2S_2O_4$, CuBr, CuI, $FeBr_2$, $FeSO_4$, Fe $(acac)_2$, AgF, and AgCl. The reaction may be performed in the presence of multiple metal salts.

In the case of using a radical initiator, the reaction between the vinylene carbonate and the compound (5-1) is preferably performed at 0° C. to 200° C., more preferably 20° C. to 150° C. In the case of heating without a radical initiator, the reaction temperature is preferably 150° C. to 300° C., more preferably 200° C. to 250° C.

When the reaction between the vinylene carbonate and the compound (5-1) is performed without a solvent or in an organic solvent, addition of water or any appropriate substance to the reaction product causes separation of the solution into two layers. A solution containing the compound (5-2) can be then obtained by collecting an organic layer by liquid separation. When the reaction is performed in water, addition of a water-insoluble organic solvent to the reaction product causes separation of the solution into two layers. A solution containing the compound (5-2) can be then obtained by collecting an organic layer by liquid separation. When the reaction is performed without a solvent, a solution containing the compound (5-2) can be obtained by removing excessive organic compounds with an evaporator, for example.

It is acceptable to add a desiccant such as magnesium sulfate, a hydrate of sodium sulfate (mirabilite), or molecular sieve to the solution containing the compound (5-2), and to filter out the desiccant and collect the solution containing the compound (5-2) as a filtrate. This solution may be subjected to the next step.

Next, the compound (5-2) is reacted with a base or metal.

This reaction can be performed in a solvent. The solvent may be any organic solvent, and may be the solvent used in the reaction for providing the compound (5-2). Alternatively, it is acceptable to distill the solvent from the solution containing the compound (5-2) and to add a solvent that is different from the solvent used in the reaction for providing the compound (5-2)), and then to react the compound (5-2) with a base or metal in this solvent. Also, it is acceptable, after performing the reaction for providing the compound (5-2) without a solvent, to distill off volatile components in the reaction solution as appropriate and to introduce a solvent required, and then to react the compound (5-2) with a base or metal in this solvent.

The base may be either an organic base or an inorganic base. Preferred among these are triethylamine, diisopropylethylamine, and tert-butoxypotassium.

The metal is preferably zinc.

The base or metal may be added to the solution containing the compound (5-2) which is collected after the reaction is quenched by adding water or any appropriate substance. Alternatively, water or any appropriate substance and the base or metal may be added at the same time to a solution obtained by reacting the vinylene carbonate and the compound (5-1). In this case, the two steps can be successively performed in the same container.

Then, the reaction can be quenched by adding an acidic aqueous solution. When the reaction between the compound (5-2) and the base or metal is performed in a water-insoluble organic solvent, addition of the acidic aqueous solution to the reaction product causes separation of the solution into two layers. A solution containing the compound (1) is then obtained by collecting an organic layer by liquid separation.

It is acceptable to add a desiccant such as magnesium sulfate, a hydrate of sodium sulfate (mirabilite), or molecular sieve to the resulting solution containing the compound (1), to filter out the desiccant and collect the solution containing the compound (1) as a filtrate, and then to concentrate the solution.

The compound (1) can be highly purified by distilling the resulting solution containing the compound (1) or sublimating the compound (1) from the solution. The purification technique is not limited to distillation or sublimation. If desired, the purification can be achieved by any known purification technique such as solvent extraction, drying, filtering, concentration, column chromatography, recrystallization, and any combination thereof.

The aforementioned novel compound is useful as a component constituting an electrolyte solution to be used in an electrochemical device such as a lithium ion secondary battery.

The electrolyte solution preferably contains the compound represented by the formula (1), more preferably further contains a solvent and an electrolyte salt. The electrolyte solution containing the compound represented by the formula (1) has a high capacity recovery and generates a small amount of gas even when stored at high temperature.

The electrolyte solution preferably contains 0.001 to 90 vol % of the compound represented by the formula (1) relative to the solvent. The amount of the compound represented by the formula (1) is more preferably 0.01 vol % or more while more preferably 60 vol % or less, still more preferably 20 vol % or less, particularly preferably 10 vol % or less.

The solvent preferably further contains at least one selected from the group consisting of fluorinated acyclic carbonates, non-fluorinated saturated cyclic carbonates, fluorinated saturated cyclic carbonates, and non-fluorinated acyclic carbonates.

The fluorinated acyclic carbonates are each an acyclic carbonate containing a fluorine atom.

The fluorinated acyclic carbonate preferably has a fluorine content of 10 to 70 mass %. The fluorine content may be calculated by:

$$\{(\text{number of fluorine atoms} \times 19)/(\text{molecular weight of fluorinated acyclic carbonate})\} \times 100 (\%)$$

based on the structural formula of the fluorinated acyclic carbonate.

Examples of the fluorinated acyclic carbonate include fluorinated acyclic carbonates represented by the formula: $Rf^1OCOORf^2$, where $Rf^1$ and $Rf^2$ are the same as or different from each other and are each a C1-C4 alkyl group or fluorine-containing alkyl group, but at least one of $Rf^1$ and $Rf^2$ is a C1-C4 fluorine-containing alkyl group.

$Rf^1$ and $Rf^2$ are the same as or different from each other and are each a C1-C4 alkyl group or a C1-C4 fluorine-containing alkyl group, but at least one of $Rf^1$ and $Rf^2$ is a C1-C4 fluorine-containing alkyl group.

The above carbon number is preferably 1 to 3 in order to achieve good compatibility with the electrolyte solution.

Examples of $Rf^1$ include $CF_3$—, $CF_3CF_2$—, $(CF_3)_2CH$—, $CF_3CH_2$—, $C_2F_5CH_2$—, $HCF_2CH_2$—, $HCF_2CF_2CH_2$—, and $CF_3CFHCF_2CH_2$—. In order to achieve high flame retardance, good rate characteristics, and good oxidation resistance, $CF_3CH_2$— and $HCF_2CH_2$— are preferred.

Examples of $Rf^2$ include $CF_3$—, $CF_3CF_2$—, $(CF_3)_2CH$—, $CF_3CH_2$—, $C_2F_5CH_2$—, $HCF_2CH_2$—, $HCF_2CF_2CH_2$—, and $CF_3CFHCF_2CH_2$—. In order to achieve high flame retardance, good rate characteristics, and good oxidation resistance, $CF_3CH_2$— and $HCF_2CH_2$— are preferred.

Specific examples of the fluorinated acyclic carbonate include fluorinated acyclic carbonates such as $CF_3CH_2OCOOCH_2CF_3$, $CF_3CH_2OCOOCH_3$, $CF_3CF_2CH_2OCOOCH_2CF_2CF_3$, and $CF_3CF_2CH_2OCOOCH_3$. Examples thereof further include compounds disclosed in JP H06-21992 A, JP 2000-327634 A, and JP 2001-256983 A. In order to achieve high effectiveness of suppressing generation of gas and improving the high-temperature storage characteristics, at least one compound selected from the group consisting of $CF_3CH_2OCOOCH_2CF_3$, $CF_3CH_2OCOOCH_3$, and $CF_3CF_2CH_2OCOOCH_2CF_2CF_3$ is preferred. The fluorine content is more preferably 20 mass % or more, still more preferably 30 mass % or more, particularly preferably 33 mass % or more. The fluorine content is more preferably 60 mass % or less, still more preferably 55 mass % or less.

Examples of the non-fluorinated saturated cyclic carbonates include ethylene carbonate (EC), propylene carbonate (PC), and butylene carbonate.

In order to achieve a high permittivity and a suitable viscosity, the non-fluorinated saturated cyclic carbonates are each preferably at least one compound selected from the group consisting of ethylene carbonate, propylene carbonate, and butylene carbonate.

For the non-fluorinated saturated cyclic carbonate, one of the above compounds may be used or two or more thereof may be used in combination.

The fluorinated saturated cyclic carbonates are each a saturated cyclic carbonate with a fluorine atom attached thereto. Specific examples thereof include a fluorinated saturated cyclic carbonate (A) represented by the following formula (A):

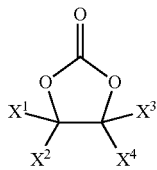

wherein $X^1$ to $X^4$ are the same as or different from each other, and are each a fluorinated alkyl group which may optionally contain —H, —CH$_3$, —F, or an ether bond, or a fluorinated alkoxy group which may optionally contain an ether bond; at least one of $X^1$ to $X^4$ is a fluorinated alkyl group which may optionally contain —F or an ether bond, or a fluorinated alkoxy group which may optionally contain an ether bond.

If the electrolyte solution contains the fluorinated saturated cyclic carbonate (A) and is applied to a lithium ion secondary battery, a stable film is formed on the negative electrode so that side reactions of the electrolyte solution on the negative electrode may sufficiently be suppressed. As a result, significantly stable, excellent charge and discharge characteristics can be achieved.

The term "ether bond" herein means a bond represented by —O—.

In order to achieve a good permittivity and oxidation resistance, one or two of $X^1$ to $X^4$ in the formula (A) is/are preferably a fluorinated alkyl group which may optionally contain —F or an ether bond or a fluorinated alkoxy group which may optionally contain an ether bond.

In anticipation of a decrease in the viscosity at low temperatures, an increase in the flash point, and improvement in the solubility of the electrolyte salt, each of $X^1$ to $X^4$ in the formula (A) is preferably —H, —F, a fluorinated alkyl group (a), a fluorinated alkyl group (b) containing an ether bond, or a fluorinated alkoxy group (c).

The fluorinated alkyl group (a) is an alkyl group in which at least one hydrogen atom is replaced by a fluorine atom. The fluorinated alkyl group (a) preferably has a carbon number of 1 to 20, more preferably 2 to 17, still more preferably 2 to 7, particularly preferably 2 to 5.

Too large a carbon number may cause poor low-temperature characteristics and low solubility of the electrolyte salt. Too small a carbon number may cause low solubility of the electrolyte salt, low discharge efficiency, and high viscosity, for example.

Examples of the fluorinated alkyl group (a) which has a carbon number of 1 include CFH$_2$—, CF$_2$H—, and CF$_3$—.

In order to achieve good solubility of the electrolyte salt, preferred examples of the fluorinated alkyl group (a) which has a carbon number of 2 or greater include fluorinated alkyl groups represented by the following formula (a-1):

$$R^1—R^2— \quad (a-1)$$

wherein $R^1$ is an alkyl group which may optionally contain a fluorine atom and which has a carbon number of 1 or greater; $R^2$ is a C1-C3 alkylene group which may optionally contain a fluorine atom; and at least one of $R^1$ and $R^2$ contains a fluorine atom.

$R^1$ and $R^2$ each may further contain an atom other than the carbon atom, hydrogen atom, and fluorine atom.

$R^1$ is an alkyl group which may optionally contain a fluorine atom and which has a carbon number of 1 or greater. $R^1$ is preferably a C1-C16 linear or branched alkyl group. The carbon number of $R^1$ is more preferably 1 to 6, still more preferably 1 to 3.

Specific examples of the linear or branched alkyl group for $R^1$ include CH$_3$—, CH$_3$CH$_2$—, CH$_3$CH$_2$CH$_2$—, CH$_3$CH$_2$CH$_2$CH$_2$—, and the groups represented by the following formulas:

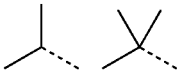

wherein the dashed lines each represent a bonding site.

If $R^1$ is a linear alkyl group containing a fluorine atom, examples thereof include CF$_3$—, CF$_3$CH$_2$—, CF$_3$CF$_2$—, CF$_3$CH$_2$CH$_2$—, CF$_3$CF$_2$CH$_2$—, CF$_3$CF$_2$CF$_2$—, CF$_3$CH$_2$CF$_2$—, CF$_3$CH$_2$CH$_2$CH$_2$—, CF$_3$CF$_2$CH$_2$CH$_2$—, CF$_3$CH$_2$CF$_2$CH$_2$—, CF$_3$CF$_2$CF$_2$CH$_2$—, CF$_3$CF$_2$CH$_2$CF$_2$—, CF$_3$CH$_2$CH$_2$CH$_2$CH$_2$—, CF$_3$CF$_2$CH$_2$CH$_2$CH$_2$—, CF$_3$CH$_2$CF$_2$CH$_2$CH$_2$—, CF$_3$CF$_2$CF$_2$CH$_2$CH$_2$—, CF$_3$CF$_2$CF$_2$CF$_2$CH$_2$—, CF$_3$CF$_2$CH$_2$CF$_2$CH$_2$—, CF$_3$CF$_2$CF$_2$CF$_2$CH$_2$CH$_2$—, CF$_3$CF$_2$CH$_2$CF$_2$CH$_2$CH$_2$—, HCF$_2$—, HCF$_2$CH$_2$—, HCF$_2$CF$_2$—, HCF$_2$CH$_2$CH$_2$—, HCF$_2$CF$_2$CH$_2$—, HCF$_2$CH$_2$CF$_2$—, HCF$_2$CF$_2$CH$_2$CH$_2$—, HCF$_2$CH$_2$CF$_2$CH$_2$—, HCF$_2$CF$_2$CF$_2$CF$_2$—, HCF$_2$CF$_2$CH$_2$CH$_2$—, HCF$_2$CH$_2$CF$_2$CH$_2$CH$_2$—, HCF$_2$CF$_2$CF$_2$CF$_2$CH$_2$—, HCF$_2$CF$_2$CF$_2$CF$_2$CH$_2$CH$_2$—, FCH$_2$—, FCH$_2$CH$_2$—, FCH$_2$CF$_2$—, FCH$_2$CF$_2$CH$_2$—, FCH$_2$CF$_2$CF$_2$—, CH$_3$CF$_2$CH$_2$—, CH$_3$CF$_2$CF$_2$—, CH$_3$CH$_2$CH$_2$—, CH$_3$CF$_2$CH$_2$CF$_2$—, CH$_3$CF$_2$CF$_2$CF$_2$—, CH$_3$CH$_2$CF$_2$CF$_2$—, CH$_3$CF$_2$CH$_2$CF$_2$CH$_2$—, CH$_3$CF$_2$CF$_2$CF$_2$CH$_2$—, CH$_3$CF$_2$CF$_2$CH$_2$CH$_2$—, CH$_3$CH$_2$CF$_2$CF$_2$CH$_2$—, CH$_3$CF$_2$CH$_2$CF$_2$CH$_2$CH$_2$—, HCFClCF$_2$CH$_2$—, HCF$_2$CFClCH$_2$—, HCF$_2$CFClCF$_2$CFClCH$_2$—, and HCFClCF$_2$CFClCF$_2$CH$_2$—.

If $R^1$ is a branched alkyl group containing a fluorine atom, preferred examples thereof include those represented by the following formulas:

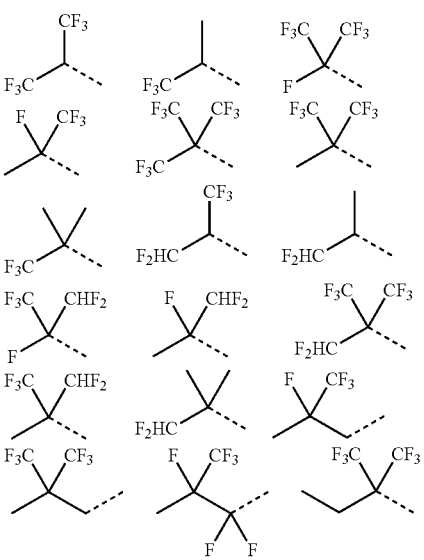

-continued

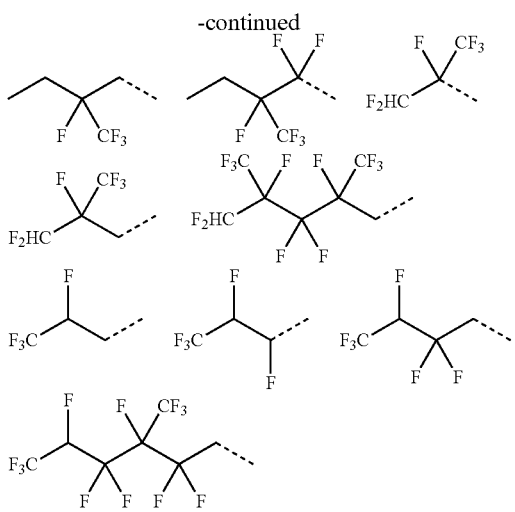
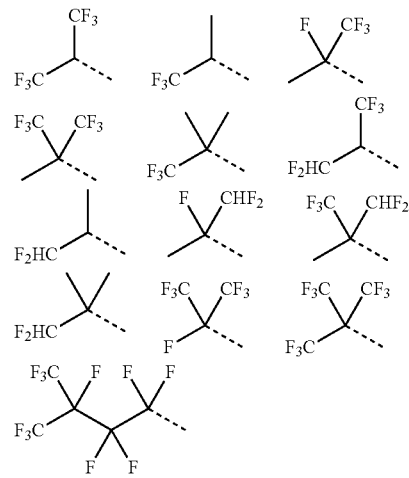

(wherein the dashed lines each represent a bonding site). If the group has a branch represented by —CH$_3$ or —CF$_3$, for example, the viscosity is likely to be high. Thus, the number of such branches is more preferably small (one) or zero.

R$^2$ is a C1-C3 alkylene group which may optionally contain a fluorine atom. R$^2$ may be a linear or branched group. Examples of a minimum structural unit constituting such a linear or branched alkylene group are shown below. R$^2$ is constituted by one or combination of these units.

(i) Linear Minimum Structural Units

—CH$_2$—, —CHF—, —CF$_2$—, —CHCl—, —CFCl—, —CCl$_2$—

(ii) Branched Minimum Structural Units (the Dashed Lines in the Formulas Each Represent a Bonding Site)

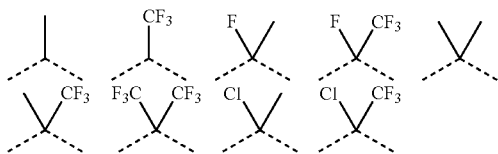

Preferred among these exemplified units are Cl-free structural units because such units are not dehydrochlorinated by a base, and thus are more stable.

If R$^2$ is a linear group, the group consists only of the above linear minimum structural unit, preferably —CH$_2$—, —CH$_2$CH$_2$—, or —CF$_2$—. In order to further improve the solubility of the electrolyte salt, —CH$_2$— or —CH$_2$CH$_2$— is more preferred.

If R$^2$ is a branched group, the group includes at least one of the above branched minimum structural units. Preferred examples thereof include those represented by the formula: —(CX$^a$X$^b$)— (wherein X$^a$ is H, F, CH$_3$, or CF$_3$; X$^b$ is CH$_3$ or CF$_3$; if X$^b$ is CF$_3$, X$^a$ is H or CH$_3$). Such groups can further improve the solubility of the electrolyte salt.

Preferred examples of the fluorinated alkyl group (a) include CF$_3$CF$_2$—, HCF$_2$CF$_2$—, H$_2$CFCF$_2$—, CH$_3$CF$_2$—, CF$_3$CF$_2$CF$_2$—, HCF$_2$CF$_2$CF$_2$—, H$_2$CFCF$_2$CF$_2$—, CH$_3$CF$_2$CF$_2$—, and those represented by the following formulas:

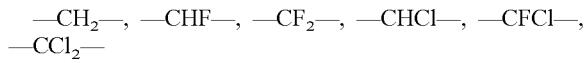

wherein the dashed lines each represent a bonding site.

The fluorinated alkyl group (b) containing an ether bond is an alkyl group which has an ether bond and in which at least one hydrogen atom is replaced by a fluorine atom. The fluorinated alkyl group (b) containing an ether bond preferably has a carbon number of 2 to 17. Too large a carbon number may cause high viscosity of the fluorinated saturated cyclic carbonate (A) and an increased number of fluorine-containing groups. Thus, the solubility of the electrolyte salt may be poor due to reduction in the permittivity, and the compatibility with other solvents may be poor. Accordingly, the carbon number of the fluorinated alkyl group (b) containing an ether bond is preferably 2 to 10, more preferably 2 to 7.

The alkylene group which constitutes the ether segment of the fluorinated alkyl group (b) containing an ether bond may be a linear or branched alkylene group. Examples of a minimum structural unit constituting such a linear or branched alkylene group are shown below.

(i) Linear Minimum Structural Units

—CH$_2$—, —CHF—, —CF$_2$—, —CHCl—, —CFCl—, —CCl$_2$—

(ii) Branched Minimum Structural Units (the Dashed Lines in the Formulas Each Represent a Bonding Site)

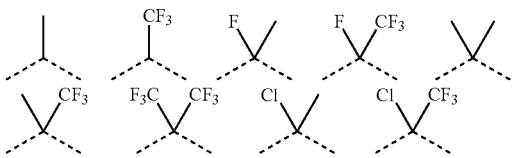

The alkylene group may be constituted by one of these minimum structural units alone, or may be constituted by multiple linear units (i), by multiple branched units (ii), or by a combination of a linear unit (i) and a branched unit (ii). Preferred specific examples thereof will be mentioned later.

Preferred among these exemplified units are Cl-free structural units because such units are not dehydrochlorinated by a base, and thus are more stable.

Still more preferred examples of the fluorinated alkyl group (b) containing an ether bond include those represented by the following formula (b-1):

R$^3$—(OR$^4$)$_{n1}$—     (b-1)

wherein R³ is preferably a C1-C6 alkyl group which may optionally contain a fluorine atom; R⁴ is preferably a C1-C4 alkylene group which may optionally contain a fluorine atom; n1 is an integer of 1 to 3; and at least one of R³ and R⁴ contains a fluorine atom.

Examples of the groups for R³ and R⁴ include the following, and any appropriate combination of these groups can provide the fluorinated alkyl group (b) containing an ether bond represented by the formula (b-1). Still, the groups are not limited thereto.

(1) R³ is preferably an alkyl group represented by the formula: $X^c{}_3C\text{—}(R^5)_{n2\text{-}}$, where three $X^c$s are the same as or different from each other, and are each H or F; R⁵ is a C1-C5 alkylene group which may optionally contain a fluorine atom; and n2 is 0 or 1.

If n2 is 0, R³ may be CH₃—, CF₃—, HCF₂—, or H₂CF—, for example.

If n2 is 1, specific examples of a linear group for R³ include CF₃CH₂—, CF₃CF₂—, CF₃CH₂CH₂—, CF₃CF₂CH₂—, CF₃CF₂CF₂—, CF₃CH₂CF₂—, CF₃CH₂CH₂CH₂—, CF₃CF₂CH₂CH₂—, CF₃CH₂CF₂CH₂—, CF₃CF₂CF₂CH₂—, CF₃CF₂CF₂CF₂—, CF₃CF₂CH₂CF₂—, CF₃CH₂CH₂CH₂CH₂—, CF₃CF₂CH₂CH₂CH₂—, CF₃CH₂CF₂CH₂CH₂—, CF₃CF₂CF₂CH₂CH₂—, CF₃CF₂CH₂CF₂CH₂—, CF₃CF₂CF₂CF₂CH₂—, CF₃CF₂CF₂CH₂CH₂—, CF₃CF₂CH₂CH₂CH₂CH₂—, CF₃CF₂CF₂CF₂CH₂CH₂—, CF₃CF₂CH₂CH₂CH₂CH₂—, HCF₂CH₂—, HCF₂CF₂—, HCF₂CH₂CH₂—, HCF₂CF₂CH₂—, HCF₂CH₂CF₂—, HCF₂CF₂CH₂CH₂—, HCF₂CH₂CF₂CH₂—, HCF₂CF₂CF₂CF₂—, HCF₂CF₂CH₂CH₂CH₂—, HCF₂CH₂CF₂CH₂CH₂—, HCF₂CF₂CF₂CF₂CH₂—, HCF₂CF₂CF₂CF₂CH₂CH₂—, FCH₂CH₂—, FCH₂CF₂—, FCH₂CF₂CH₂—, FCH₂CF₂CH₂—, CH₃CF₂—, CH₃CH₂—, CH₃CF₂CH₂—, CH₃CF₂CF₂—, CH₃CH₂CH₂—, CH₃CF₂CH₂CF₂—, CH₃CF₂CF₂CF₂—, CH₃CH₂CF₂CF₂—, CH₃CH₂CH₂CH₂—, CH₃CF₂CH₂CF₂CH₂—, CH₃CF₂CF₂CF₂CH₂—, CH₃CF₂CF₂CH₂CH₂—, CH₃CH₂CF₂CF₂CH₂—, CH₃CH₂CF₂CF₂CH₂CH₂—, and CH₃CF₂CH₂CF₂CH₂CH₂—.

If n2 is 1, examples of a branched group for R³ include those represented by the following formulas:

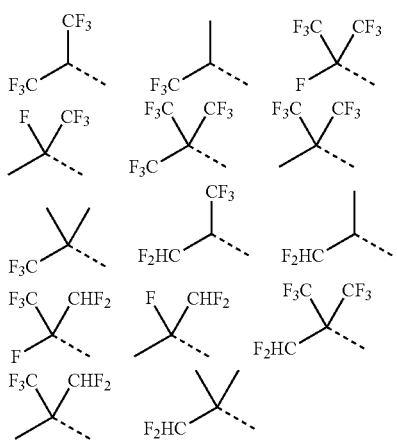

wherein the dashed lines each represent a bonding site.

If the group for R³ has a branch such as —CH₃ or —CF₃, the viscosity is likely to be high. Thus, the group for R³ is more preferably a linear group.

(2) In the segment —(OR⁴)$_{n1}$— of the formula (b-1), n1 is an integer of 1 to 3, preferably 1 or 2. If n1 is 2 or 3, R⁴s may be the same as or different from each other.

Preferred specific examples of the group for R⁴ include the following linear or branched groups.

Examples of the linear groups include —CH₂—, —CHF—, —CF₂—, —CH₂CH₂—, —CF₂CH₂—, —CF₂CF₂—, —CH₂CF₂—, —CH₂CH₂CH₂—, —CH₂CH₂CF₂—, —CH₂CF₂CH₂—, —CH₂CF₂CF₂—, —CF₂CH₂CH₂—, —CF₂CF₂CH₂—, —CF₂CH₂CF₂—, and —CF₂CF₂CF₂—.

Examples of the branched groups include those represented by the following formulas:

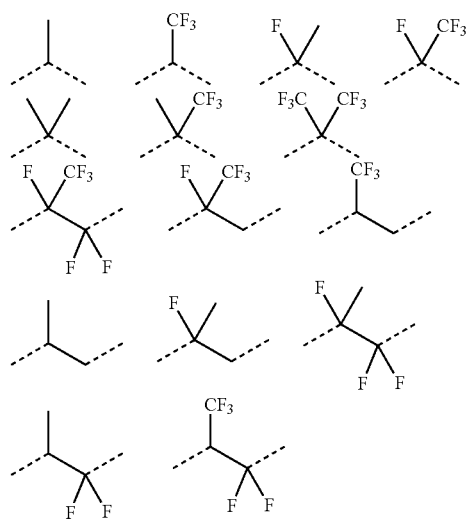

wherein the dashed lines each represent a bonding site.

The fluorinated alkoxy group (c) is an alkoxy group in which at least one hydrogen atom is replaced by a fluorine atom. The fluorinated alkoxy group (c) preferably has a carbon number of 1 to 17. The carbon number is more preferably 1 to 6.

The fluorinated alkoxy group (c) is particularly preferably a fluorinated alkoxy group represented by the formula: $X^d{}_3C\text{—}(R^6)_{n3}\text{—}O\text{—}$ (wherein three $X^d$s are the same as or different from each other, and are each H or F; R⁶ is preferably a C1-C5 alkylene group which may optionally contain a fluorine atom; n3 is 0 or 1; and any of the three $X^d$s contains a fluorine atom).

Specific examples of the fluorinated alkoxy group (c) include fluorinated alkoxy groups in which an oxygen atom is bonded to an end of the alkyl group for R¹ in the formula (a-1).

The fluorinated alkyl group (a), the fluorinated alkyl group (b) containing an ether bond, and the fluorinated alkoxy group (c) in the fluorinated saturated cyclic carbonate (A) each preferably have a fluorine content of 10 mass % or more. Too low a fluorine content may fail to sufficiently achieve an effect of increasing the flash point. Thus, the fluorine content is more preferably 20 mass % or more, still more preferably 30 mass % or more. The upper limit thereof is usually 85 mass %.

The fluorine content of each of the fluorinated alkyl group (a), the fluorinated alkyl group (b) containing an ether bond, and the fluorinated alkoxy group (c) is a value calculated by:

{(Number of fluorine atoms×19)/(formula weight of the group)}×100(%)

based on the corresponding structural formula.

In order to achieve a good permittivity and oxidation resistance, the fluorine content in the whole fluorinated saturated cyclic carbonate (A) is preferably 5 mass % or more, more preferably 10 mass % or more. The upper limit thereof is usually 76 mass %.

The fluorine content in the whole fluorinated saturated cyclic carbonate (A) is a value calculated by:

{(Number of fluorine atoms×19)/(molecular weight of fluorinated saturated cyclic carbonate (A))}× 100(%)

based on the structural formula of the fluorinated saturated cyclic carbonate (A).

Specific examples of the fluorinated saturated cyclic carbonate (A) include the following.

Those represented by the following formulas:

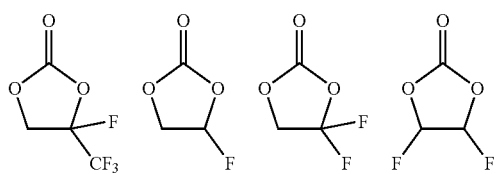

may be mentioned as specific examples of the fluorinated saturated cyclic carbonate (A) represented by the formula (A) in which at least one of $X^1$ to $X^4$ is —F. These compounds have a high withstand voltage and give good solubility of the electrolyte salt.

Alternatively, those represented by the following formulas:

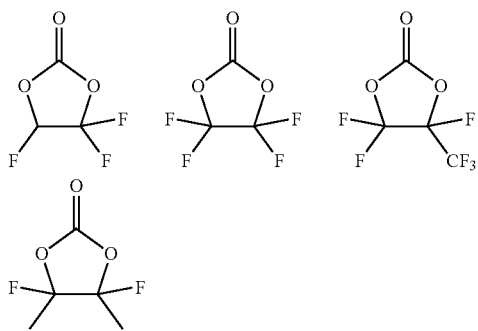

may also be used.

Those represented by the following formulas:

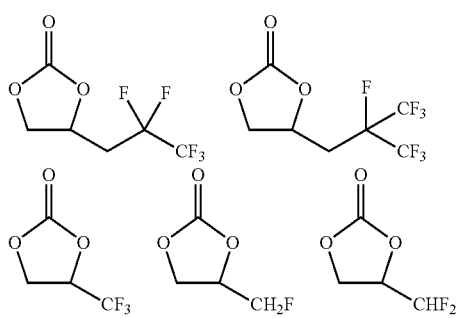

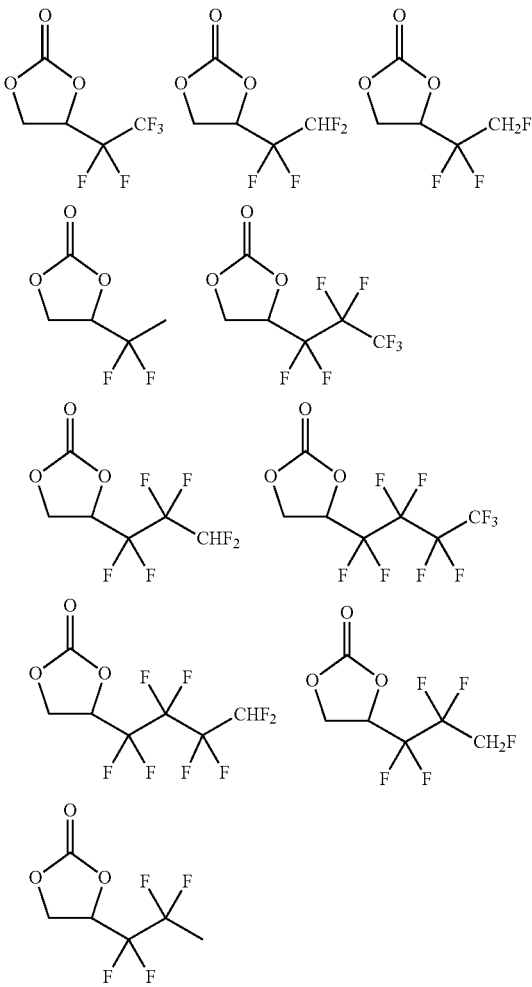

may be mentioned as specific examples of the fluorinated saturated cyclic carbonate (A) represented by the formula (A) in which at least one of $X^1$ to $X^4$ is a fluorinated alkyl group (a) and the others thereof are —H.

Those represented by the following formulas:

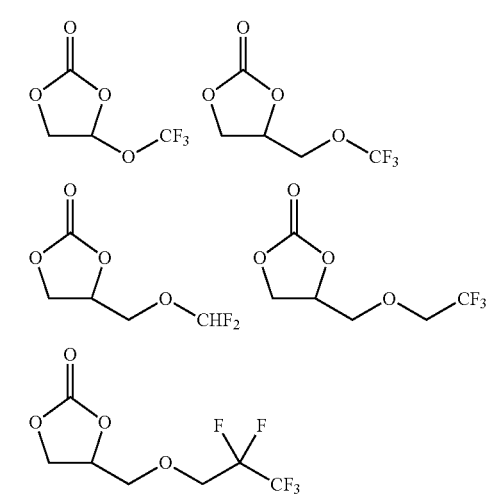

-continued
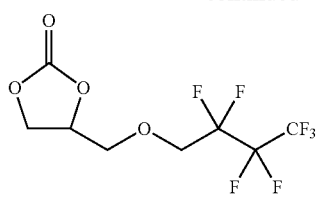
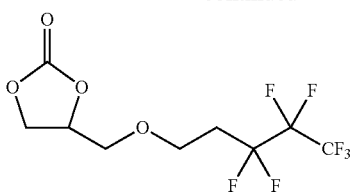
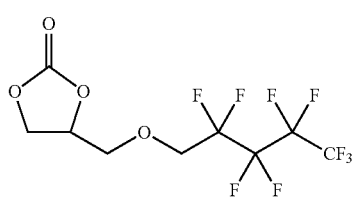
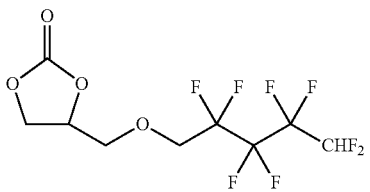
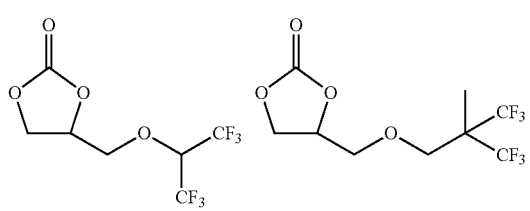
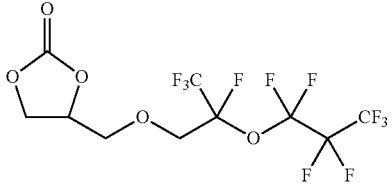
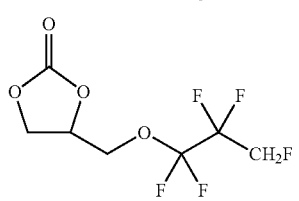
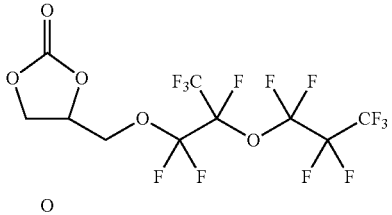
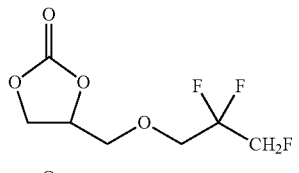
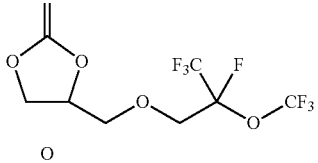
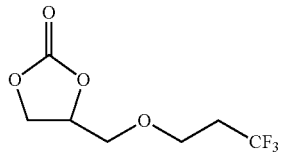
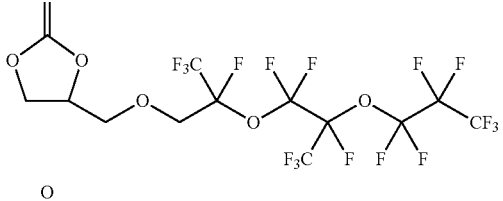
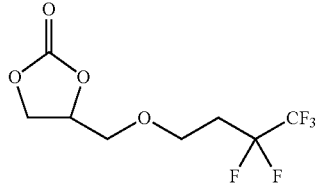
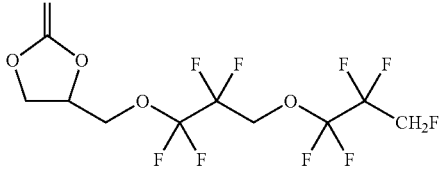
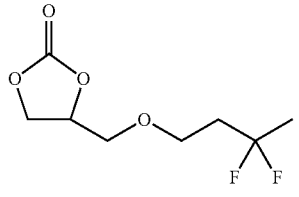
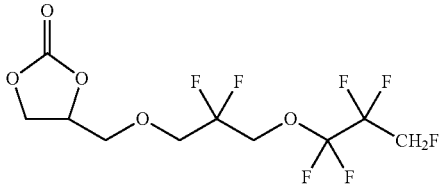
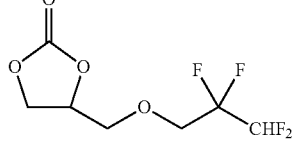
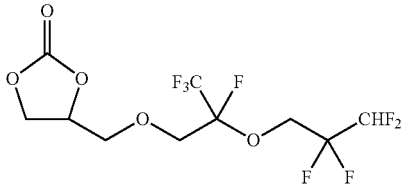

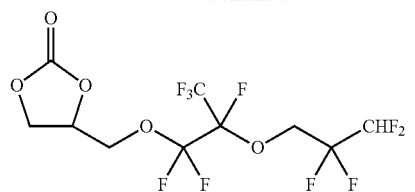
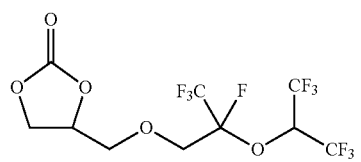
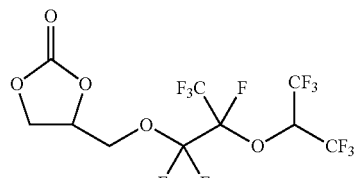
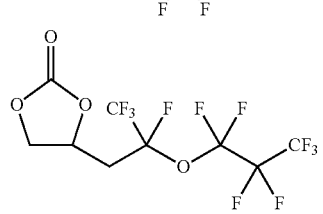
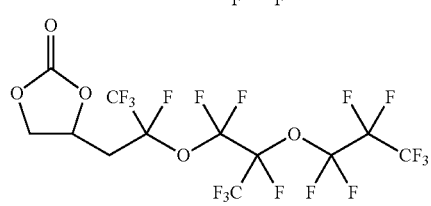
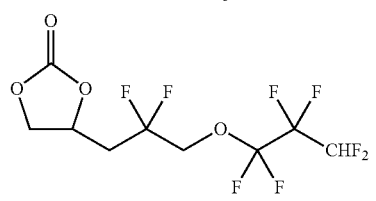
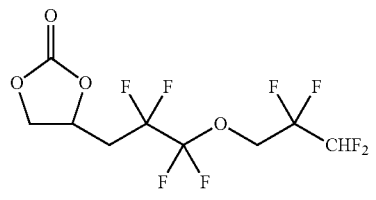
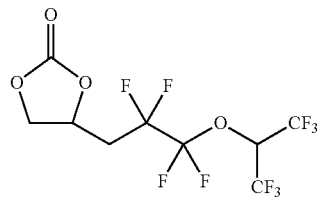
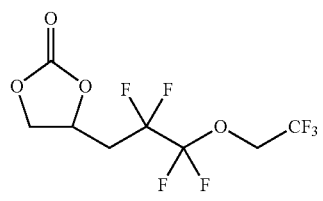
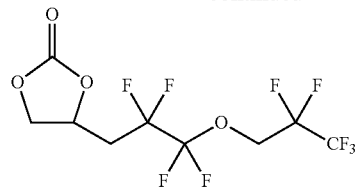
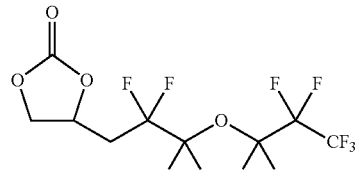
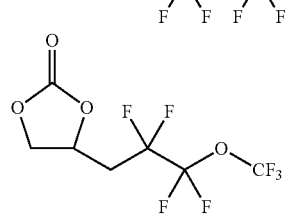
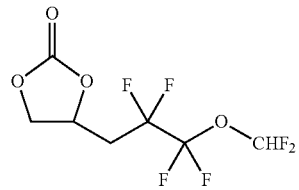
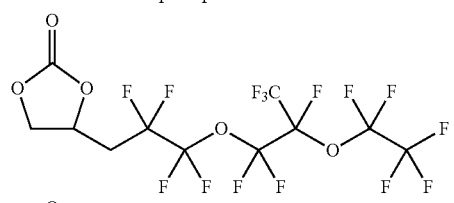
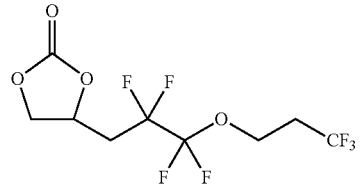
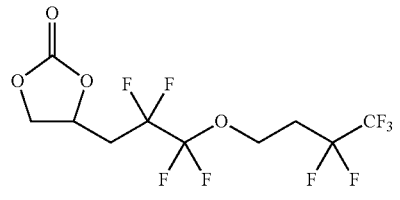
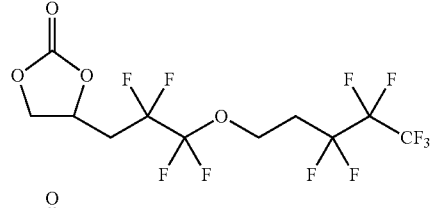
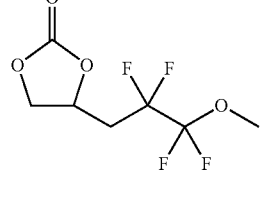

may be mentioned as specific examples of the fluorinated saturated cyclic carbonate (A) represented by the formula (A) in which at least one of $X^1$ to $X^4$ is a fluorinated alkyl group (b) containing an ether bond or a fluorinated alkoxy group (c) and the others thereof are —H.

The fluorinated saturated cyclic carbonate (A) is not limited to the above specific examples. One of the above fluorinated saturated cyclic carbonates (A) may be used alone, or two or more thereof may be used in any combination at any ratio. A preferred amount of the fluorinated saturated cyclic carbonate will be mentioned later, and such a preferred amount corresponds to a preferred amount of the fluorinated saturated cyclic carbonate (A).

Preferred as the fluorinated saturated cyclic carbonate (A) are fluoroethylene carbonate and difluoroethylene carbonate.

Examples of the non-fluorinated acyclic carbonate include hydrocarbon acyclic carbonates such as $CH_3OCOOCH_3$ (dimethyl carbonate: DMC), $CH_3CH_2OCOOCH_2CH_3$ (diethyl carbonate: DEC), $CH_3CH_2OCOOCH_3$ (ethyl methyl carbonate: EMC), $CH_3OCOOCH_2CH_2CH_3$ (methyl propyl carbonate), methyl butyl carbonate, ethyl propyl carbonate, and ethyl butyl carbonate. Preferred among these is at least one compound selected from the group consisting of dimethyl carbonate, ethyl methyl carbonate, diethyl carbonate, methyl propyl carbonate, methyl butyl carbonate, ethyl propyl carbonate, and ethyl butyl carbonate.

The solvent preferably contains 10 to 99.99 vol %, more preferably 40 vol % or more, still more preferably 50 vol % or more, particularly preferably 70 vol % or more, while more preferably 99.9 vol % or less, still more preferably 99.5 vol % or less, further more preferably 99 vol % or less, particularly preferably 96 vol % or less, most preferably 80 vol % or less, in total of the non-fluorinated saturated cyclic carbonate, fluorinated saturated cyclic carbonate, non-fluorinated acyclic carbonate, and fluorinated acyclic carbonate.

The solvent preferably contains at least one saturated cyclic carbonate selected from the group consisting of non-fluorinated saturated cyclic carbonates and fluorinated saturated cyclic carbonates and at least one acyclic carbonate selected from the group consisting of non-fluorinated acyclic carbonates and fluorinated acyclic carbonates.

The volume ratio of the saturated cyclic carbonate and the acyclic carbonate is preferably 10/90 to 90/10, more preferably 30/70 or higher, while more preferably 70/30 or lower.

The electrolyte solution contains an electrolyte salt.

Any electrolyte salt usable for electrolyte solutions for electrochemical devices such as secondary batteries and electric double-layer capacitors may be used. Preferred is a lithium salt.

Examples of the lithium salt include inorganic lithium salts such as $LiClO_4$, $LiPF_6$, and $LiBF_4$; and fluoroorganic acid lithium salts such as $LiSO_3CF_3$, $LiN(SO_2CF_3)_2$, $LiN(SO_2C_2F_5)_2$, $LiN(SO_2CF_3)(SO_2C_4F_9)$, $LiC(SO_2CF_3)_3$, $LiPF_4(CF_3)_2$, $LiPF_4(C_2F_5)_2$, $LiPF_4(SO_2CF_3)_2$, $LiPF_4(SO_2C_2F_5)_2$, $LiBF_2(CF_3)_2$, $LiBF_2(C_2F_5)_2$, $LiBF_2(SO_2CF_3)_2$, $LiBF_2(SO_2C_2F_5)_2$, lithium difluoro(oxalato)borate, lithium bis(oxalato)borate, and salts represented by the formula: $LiPF_a(C_nF_{2n+1})_{6-a}$ (wherein a is an integer of 0 to 5; and n is an integer of 1 to 6). These may be used alone or in combination of two or more.

In order to suppress degradation of the electrolyte solution after high-temperature storage, the lithium salt is particularly preferably at least one selected from the group consisting of $LiPF_6$, $LiBF_4$, $LiSO_3CF_3$, $LiN(SO_2CF_3)_2$, $LiN(SO_2C_2F_5)_2$, lithium difluoro(oxalato)borate, lithium bis(oxalato)borate, and salts represented by the formula: $LiPF_a(C_nF_{2n+1})_{6-a}$, where a is an integer of 0 to 5; and n is an integer of 1 to 6.

Examples of the salts represented by the formula: $LiPF_a(C_nF_{2n+1})_{6-a}$ include $LiPF_3(CF_3)_3$, $LiPF_3(C_2F_5)_3$, $LiPF_3(C_3F_7)_3$, $LiPF_3(C_4F_9)_3$, $LiPF_4(CF_3)_2$, $LiPF_4(C_2F_5)_2$, $LiPF_4(C_3F_7)_2$, and $LiPF_4(C_4F_9)_2$, where the alkyl group represented by $C_3F_7$ or $C_4F_9$ in the formula may be either linear or branched.

The concentration of the electrolyte salt in the electrolyte solution is preferably 0.5 to 3 mol/L. If the concentration thereof is outside this range, the electrolyte solution tends to have a low electric conductivity and the battery performance tends to be impaired.

The concentration of the electrolyte salt is more preferably 0.9 mol/L or more and 1.5 mol/L or less.

The electrolyte salt is preferably an ammonium salt.

Examples of the ammonium salt include the following salts (IIa) to (IIe).

(IIa) Tetraalkyl Quaternary Ammonium Salts

Preferred examples thereof include tetraalkyl quaternary ammonium salts represented by the following formula (IIa):

(IIa)

(wherein $R^{1a}$, $R^{2a}$, $R^{3a}$, and $R^{4a}$ are the same as or different from each other, and are each a C1-C6 alkyl group which may optionally contain an ether bond; and $X^-$ is an anion). In order to improve the oxidation resistance, part or all of the hydrogen atoms in the ammonium salt may also preferably be replaced by a fluorine atom and/or a C1-C4 fluorine-containing alkyl group.

Preferred specific examples of the tetraalkyl quaternary ammonium salts include tetraalkyl quaternary ammonium salts represented by the following formula (IIa-1):

(IIa-1)

(wherein $R^{1a}$, $R^{2a}$, and $X^-$ are defined in the same manner as mentioned above; x and y are the same as or different from each other, and are each an integer of 0 to 4, where x+y=4), and alkyl ether group-containing trialkyl ammonium salts represented by the following formula (IIa-2):

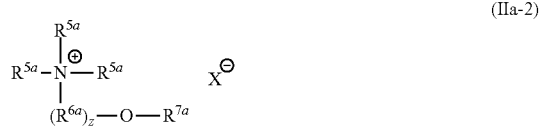

(IIa-2)

(wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion). Introduction of an alkyl ether group may lead to reduction in the viscosity.

The anion $X^-$ may be either an inorganic anion or an organic anion. Examples of the inorganic anion include $AlCl_4^-$, $BF_4^-$, $PF_6^-$, $AsF_6^-$, $TaF_6^-$, $I^-$, and $SbF_6^-$. Examples of the organic anion include $CF_3COO^-$, $CF_3SO_3^-$, $(CF_3SO_2)_2N^-$, and $(C_2F_5SO_2)_2N^-$.

In order to achieve good oxidation resistance and ionic dissociation, $BF_4^-$, $PF_6^-$, $AsF_6^-$, and $SbF_6^-$ are preferred.

Preferred specific examples of the tetraalkyl quaternary ammonium salts include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, $Et_3MeNC_4F_9SO_3$, and N,N-diethyl-N-methyl-N-(2-methoxyethyl)ammonium salts. Particularly preferred examples thereof include $Et_4NBF_4$, $Et_4NPF_6$, $Et_4NSbF_6$, $Et_4NAsF_6$, $Et_3MeNBF_4$, and N,N-diethyl-N-methyl-N-(2-methoxyethyl)ammonium salts.

(IIb) Spirocyclic Bipyrrolidinium Salts

Preferred examples thereof include spirocyclic bipyrrolidinium salts represented by the following formula (IIb-1):

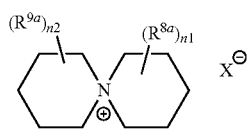

(IIb-1)

(wherein $R_{8a}$ and $R^{9a}$ are the same as or different from each other, and are each a C1-C4 alkyl group; $X^+$ is an anion; n1 is an integer of 0 to 5; and n2 is an integer of 0 to 5); spirocyclic bipyrrolidinium salts represented by the following formula (IIb-2):

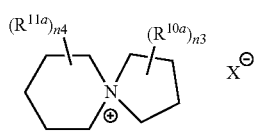

(IIb-2)

(wherein $R^{10a}$ and $R^{11a}$ are the same as or different from each other, and are each a C1-C4 alkyl group; $X^-$ is an anion; n3 is an integer of 0 to 5; and n4 is an integer of 0 to 5); and spirocyclic bipyrrolidinium salts represented by the following formula (IIb-3):

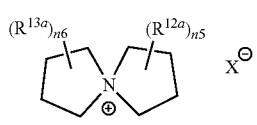

(IIb-3)

(wherein $R^{12a}$ and $R^{13a}$ are the same as or different from each other, and are each a C1-C4 alkyl group; $X^-$ is an anion; n5 is an integer of 0 to 5; and n6 is an integer of 0 to 5). In order to improve the oxidation resistance, part or all of the hydrogen atoms in the spirocyclic bipyrrolidinium salt may also preferably be replaced by a fluorine atom and/or a C1-C4 fluorine-containing alkyl group.

Preferred specific examples of the anion $X^-$ are the same as those mentioned for the salts (IIa). In order to achieve good dissociation and a low internal resistance under high voltage, $BF_4^-$, $PF_6^-$, $(CF_3SO_2)_2N^-$, or $(C_2F_5SO_2)_2N^-$ is preferred.

For example, those represented by the following formulas:

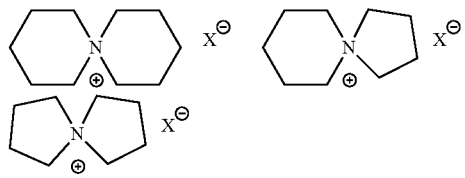

may be mentioned as preferred specific examples of the spirocyclic bipyrrolidinium salts.

These spirocyclic bipyrrolidinium salts have excellent solubility in a solvent, oxidation resistance, and ion conductivity.

(IIc) Imidazolium Salts

Preferred examples thereof include imidazolium salts represented by the following formula (IIc):

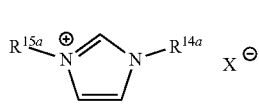

(IIc)

(wherein $R^{14a}$ and $R^{15a}$ are the same as or different from each other, and are each a C1-C6 alkyl group; and $X^-$ is an anion). In order to improve the oxidation resistance, part or all of the hydrogen atoms in the imidazolium salt may also preferably be replaced by a fluorine atom and/or a C1-C4 fluorine-containing alkyl group.

Preferred specific examples of the anion $X^-$ are the same as those mentioned for the salts (IIa).

For example, those represented by the following formula:

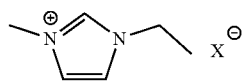

may be mentioned as a preferred specific example of the imidazolium salts.

This imidazolium salt is excellent in that it has low viscosity and good solubility.

(IId): N-Alkylpyridinium Salts

Preferred examples thereof include N-alkylpyridinium salts represented by the following formula (IId):

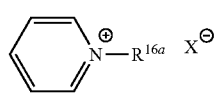

(IId)

(wherein $R^{16a}$ is a C1-C6 alkyl group; and $X^-$ is an anion). In order to improve the oxidation resistance, part or all of the hydrogen atoms in the N-alkylpyridinium salt may also preferably be replaced by a fluorine atom and/or a C1-C4 fluorine-containing alkyl group.

Preferred specific examples of the anion $X^-$ are the same as those mentioned for the salts (IIa).

For example, those represented by the following formulas:

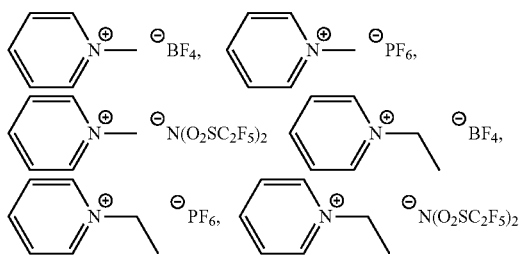

may be mentioned as preferred specific examples of the N-alkylpyridinium salts.

These N-alkylpyridinium salts are excellent in that they have low viscosity and good solubility.

(IIe) N,N-Dialkylpyrrolidinium Salts

Preferred examples thereof include N,N-dialkylpyrrolidinium salts represented by the following formula (IIe):

(wherein $R^{17a}$ and $R^{18a}$ are the same as or different from each other, and are each a C1-C6 alkyl group; and $X^-$ is an anion). In order to improve the oxidation resistance, part or all of the hydrogen atoms in the N,N-dialkylpyrrolidinium salt may also preferably be replaced by a fluorine atom and/or a C1-C4 fluorine-containing alkyl group.

Preferred specific examples of the anion $X^-$ are the same as those mentioned for the salts (IIa).

For example, those represented by the following formulas:

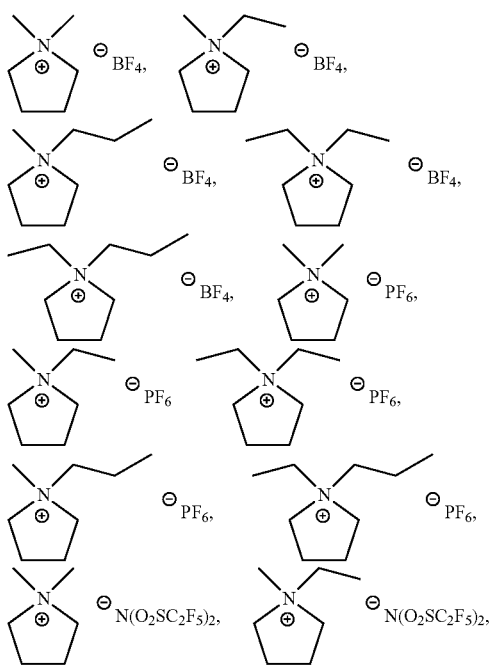

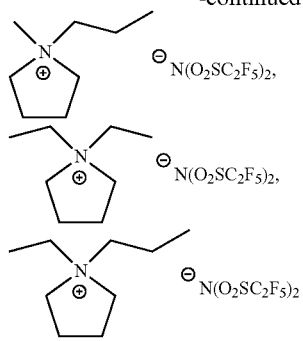

may be mentioned as preferred specific examples of the N,N-dialkylpyrrolidinium salts.

These N,N-dialkylpyrrolidinium salts are excellent in that they have low viscosity and good solubility.

Preferred among these ammonium salts are those represented by any of the formulas (IIa), (IIb), and (IIc) because they have good solubility, oxidation resistance, and ion conductivity. More preferred are those represented by the following formulas:

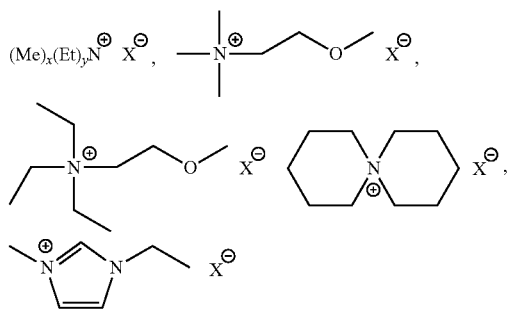

wherein Me is a methyl group; Et is an ethyl group; and $X^-$, x, and y are defined in the same manner as in the formula (IIa-1).

Another lithium salt may be used as the electrolyte salt. Preferred examples thereof include $LiAsF_6$, $LiSbF_6$, and $LiN(SO_2C_2H_5)_2$.

In order to further increase the capacity, a magnesium salt may be used. Preferred examples of the magnesium salt include $Mg(ClO_4)_2$ and $Mg(OOC_2H_5)_2$.

If the electrolyte salt is any of the above ammonium salts, the concentration thereof is preferably 0.6 mol/L or higher. If the concentration thereof is lower than 0.6 mol/L, not only the low-temperature characteristics may be poor but also the initial internal resistance may be high. The concentration of the electrolyte salt is more preferably 0.9 mol/L or higher.

For good low-temperature characteristics, the upper limit of the concentration is preferably 3.0 mol/L or lower, more preferably 2.0 mol/L or lower.

If the ammonium salt is triethyl methyl ammonium tetrafluoroborate ($TEMABF_4$), the concentration thereof is preferably 0.8 to 1.9 mol/L in order to achieve excellent low-temperature characteristics.

If the ammonium salt is spirobipyrrolidinium tetrafluoroborate ($SBPBF_4$), the concentration thereof is preferably 0.7 to 2.0 mol/L.

The electrolyte solution preferably further includes polyethylene oxide that has a weight average molecular weight of 2000 to 4000 and contains —OH, —OCOOH, or —COOH at an end.

Containing such a compound improves the stability at the interfaces between the electrolyte solution and the respective electrodes, and thus can improve the battery characteristics.

Examples of the polyethylene oxide include polyethylene oxide monool, polyethylene oxide carboxylate, polyethylene oxide diol, polyethylene oxide dicarboxylate, polyethylene oxide triol, and polyethylene oxide tricarboxylate. These may be used alone or in combination of two or more.

In order to achieve good battery characteristics, a mixture of polyethylene oxide monool and polyethylene oxide diol and a mixture of polyethylene oxide carboxylate and polyethylene oxide dicarboxylate are preferred.

Polyethylene oxide having too small a weight average molecular weight may be easily oxidatively decomposed. The weight average molecular weight is more preferably 3000 to 4000.

The weight average molecular weight can be determined in terms of polystyrene equivalent by gel permeation chromatography (GPC).

The amount of the polyethylene oxide is preferably $1 \times 10^{-6}$ to $1 \times 10^{-2}$ mol/kg in the electrolyte solution. Too small an amount of the polyethylene oxide may impair the battery characteristics.

The amount of the polyethylene oxide is more preferably $5 \times 10^{-6}$ mol/kg or more.

The electrolyte solution preferably further contains, as an additive, at least one selected from the group consisting of unsaturated cyclic carbonates (excluding the compounds represented by the formula (1)), fluorinated saturated cyclic carbonates, and cyclic sulfonic acid compounds. Containing any of these compounds suppresses degradation of the battery characteristics.

The unsaturated cyclic carbonates are each a cyclic carbonate having an unsaturated bond, i.e., a cyclic carbonate having at least one carbon-carbon unsaturated bond in the molecule. Specific examples thereof include vinylene carbonate compounds such as vinylene carbonate, methyl vinylene carbonate, ethyl vinylene carbonate, 4,5-dimethyl vinylene carbonate, and 4,5-diethyl vinylene carbonate; and vinyl ethylene carbonate compounds such as 4-vinyl ethylene carbonate (VEC), 4-methyl-4-vinyl ethylene carbonate, 4-ethyl-4-vinyl ethylene carbonate, 4-n-propyl-4-vinyl ethylene carbonate, 5-methyl-4-vinyl ethylene carbonate, 4,4-divinyl ethylene carbonate, 4,5-divinyl ethylene carbonate, 4,4-dimethyl-5-methylene ethylene carbonate, and 4,4-diethyl-5-methylene ethylene carbonate. Preferred among these is vinylene carbonate, 4-vinyl ethylene carbonate, 4-methyl-4-vinyl ethylene carbonate, or 4,5-divinyl ethylene carbonate, and particularly preferred is vinylene carbonate or 4-vinyl ethylene carbonate.

The unsaturated cyclic carbonate may have any molecular weight that does not significantly deteriorate the performance of the electrolyte solution. The molecular weight is preferably 50 or higher and 250 or lower. The unsaturated cyclic carbonate having a molecular weight within this range is likely to ensure the solubility of the unsaturated cyclic carbonate in the electrolyte solution and to enable sufficient achievement of the performance of the electrolyte solution. The molecular weight of the unsaturated cyclic carbonate is more preferably 80 or higher, while more preferably 150 or lower.

The unsaturated cyclic carbonate may also be preferably a fluorinated unsaturated cyclic carbonate.

The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives and fluorinated ethylene carbonate derivatives substituted with a substituent containing an aromatic ring or a carbon-carbon double bond.

Examples of the fluorinated vinylene carbonate derivatives include 4-fluorovinylene carbonate, 4-fluoro-5-methyl vinylene carbonate, 4-fluoro-5-phenyl vinylene carbonate, 4-allyl-5-fluorovinylene carbonate, and 4-fluoro-5-vinyl vinylene carbonate.

Examples of the fluorinated ethylene carbonate derivatives substituted with a substituent containing an aromatic ring or a carbon-carbon double bond include 4-fluoro-4-vinyl ethylene carbonate, 4-fluoro-4-allyl ethylene carbonate, 4-fluoro-5-vinyl ethylene carbonate, 4-fluoro-5-allyl ethylene carbonate, 4,4-difluoro-4-vinyl ethylene carbonate, 4,4-difluoro-4-allyl ethylene carbonate, 4,5-difluoro-4-vinyl ethylene carbonate, 4,5-difluoro-4-allyl ethylene carbonate, 4-fluoro-4,5-divinyl ethylene carbonate, 4-fluoro-4,5-diallyl ethylene carbonate, 4,5-difluoro-4,5-divinyl ethylene carbonate, 4,5-difluoro-4,5-diallyl ethylene carbonate, 4-fluoro-4-phenyl ethylene carbonate, 4-fluoro-5-phenyl ethylene carbonate, 4,4-difluoro-5-phenyl ethylene carbonate, and 4,5-difluoro-4-phenyl ethylene carbonate.

The fluorinated unsaturated cyclic carbonate may have any molecular weight that does not significantly deteriorate the performance of the electrolyte solution. The molecular weight is preferably 50 or higher and 500 or lower. The fluorinated unsaturated cyclic carbonate having a molecular weight within this range is likely to ensure the solubility of the fluorinated unsaturated cyclic carbonate in the electrolyte solution and to enable sufficient achievement of the performance of the electrolyte solution.

The unsaturated cyclic carbonates may be used alone or in any combination of two or more at any ratio.

Examples of the fluorinated saturated cyclic carbonate include compounds mentioned as examples of the fluorinated saturated cyclic carbonates usable for the solvent.

Examples of the cyclic sulfonic acid compounds include 1,3-propane sultone, 1,4-butane sultone, 1-fluoro-1,3-propane sultone, 2-fluoro-1,3-propane sultone, and 3-fluoro-1,3-propane sultone.

In order to improve the high-temperature characteristics, the electrolyte solution preferably contains 1,3-propane sultone and/or 1,4-butane sultone.

If at least one compound selected from the group consisting of the unsaturated cyclic carbonates, the fluorinated saturated cyclic carbonates, and the cyclic sulfonic acid compounds is used as an additive, the amount thereof in the electrolyte solution is preferably 0.1 to 10 mass %, more preferably 1 mass % or more, while more preferably 5 mass % or less.

The electrolyte solution may further contain any other solvents or additives such as a cyclic or acyclic carboxylate, an ether compound, a nitrogen-containing compound, a boron-containing compound, an organic silicon-containing compound, a fireproof agent (a flame retardant), a surfactant, an additive for increasing the permittivity, an improver for cycle characteristics and rate characteristics, and an overcharge inhibitor, to the extent that the performance of the electrolyte solution is not impaired.

Examples of the cyclic carboxylate include those having 3 to 12 carbon atoms in total in the structural formula. Specific examples thereof include gamma-butyrolactone, gamma-valerolactone, gamma-caprolactone, and epsilon-caprolactone. Particularly preferred is gamma-butyrolactone because it can improve the battery characteristics owing to improvement in the degree of dissociation of lithium ions.

In general, the amount of the cyclic carboxylate is preferably 0.1 mass % or more, more preferably 1 mass % or more, in 100 mass % of the electrolyte solution. The cyclic carboxylate in an amount within this range is likely to improve the electric conductivity of the electrolyte solution, and thus to improve the large-current discharge characteristics of an electrolyte battery. The amount of the cyclic carboxylate is also preferably 10 mass % or less, more preferably 5 mass % or less. Such an upper limit may make it easy to give a viscosity within an appropriate range to the electrolyte solution, to avoid a reduction in the electric conductivity, to suppress an increase in the resistance of the negative electrode, and to give large-current discharge characteristics within a favorable range to an electrolyte battery.

A fluorinated cyclic carboxylate (fluorolactone) may also suitably be used as the cyclic carboxylate. Examples of the fluorolactone include fluorolactones represented by the following formula (C):

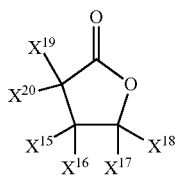

(C)

wherein $X^{15}$ to $X^{20}$ are the same as or different from each other, and are each —H, —F, —Cl, —CH$_3$, or a fluorinated alkyl group; and at least one of $X^{15}$ to $X^{20}$ is a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. In order to achieve high oxidation resistance and an effect of improving the safety, —CH$_2$CF$_3$ and —CH$_2$CF$_2$CF$_3$ are preferred.

One of $X^{15}$ to $X^{20}$ or a plurality thereof may be replaced by —H, —F, —Cl, —CH$_3$, or a fluorinated alkyl group only when at least one of $X^{15}$ to $X^{20}$ is a fluorinated alkyl group. In order to achieve good solubility of the electrolyte salt, the number of substituents is preferably 1 to 3, more preferably 1 or 2.

The substitution may be at any of the above sites in the fluorinated alkyl group. In order to achieve a good synthesizing yield, the substitution site is preferably $X^{17}$ and/or $X^{18}$. In particular, $X^{17}$ or $X^{18}$ is preferably a fluorinated alkyl group, especially, —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In order to achieve good solubility of the electrolyte salt, —H is preferred.

In addition to those represented by the above formula, the fluorolactone may also be a fluorolactone represented by the following formula (D):

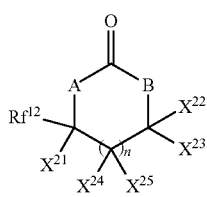

(D)

wherein one of A and B is CX$^{26}$X$^{27}$ (where X$^{26}$ and X$^{27}$ are the same as or different from each other, and are each —H, —F, —Cl, —CF$_3$, —CH$_3$, or an alkylene group in which a hydrogen atom may optionally be replaced by a halogen atom and which may optionally has a hetero atom in the chain) and the other is an oxygen atom; Rf$^{12}$ is a fluorinated alkyl group or fluorinated alkoxy group which may optionally contain an ether bond; $X^{21}$ and $X^{22}$ are the same as or different from each other, and are each —H, —F, —Cl, —CF$_3$, or CH$_3$; $X^{23}$ to $X^{25}$ are the same as or different from each other, and are each —H, —F, —Cl, or an alkyl group in which a hydrogen atom may optionally be replaced by a halogen atom and which may optionally contain a hetero atom in the chain; and n=0 or 1.

Preferred examples of the fluorolactone represented by the formula (D) include 5-membered ring structures represented by the following formula (E):

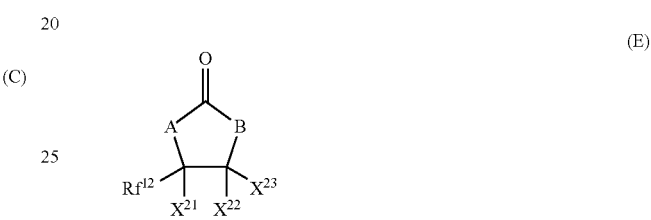

(E)

(wherein A, B, Rf$^{12}$, $X^{21}$, $X^{22}$, and $X^{23}$ are defined in the same manner as in the formula (D)) because they are easily synthesized and have good chemical stability. Further, in relation to the combination of A and B, fluorolactones represented by the following formula (F):

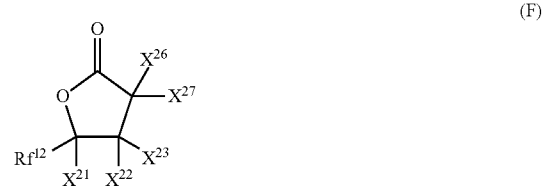

(F)

(wherein Rf$^{12}$, $X^{21}$, $X^{22}$, $X^{23}$, $X^{26}$, and $X^{27}$ are defined in the same manner as in the formula (D)) and fluorolactones represented by the following formula (G):

(G)

(wherein Rf$^{12}$, $X^{21}$, $X^{22}$, $X^{23}$, $X^{26}$, and $X^{27}$ are defined in the same manner as in the formula (D)) may be mentioned.

In order to particularly achieve excellent characteristics such as a high permittivity and a high withstand voltage, and to improve the characteristics of the electrolyte solution in the present invention, for example, to achieve good solubility of the electrolyte salt and to well reduce the internal resistance, those represented by the following formulas:

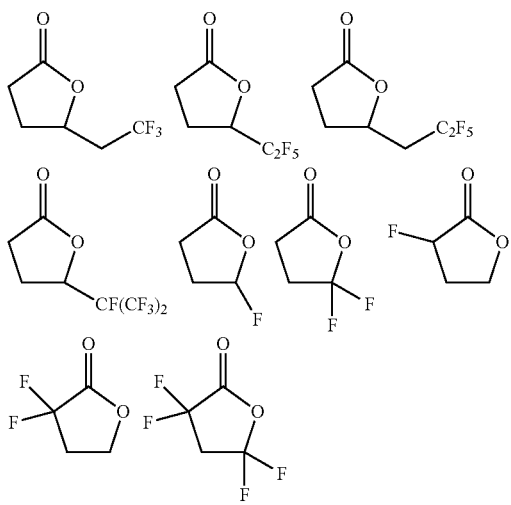

may be mentioned.

Containing a fluorinated cyclic carboxylate leads to effects of, for example, improving the ion conductivity, improving the safety, and improving the stability at high temperature.

Examples of the acyclic carboxylate include those having three to seven carbon atoms in total in the structural formula. Specific examples thereof include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

In order to improve the ion conductivity owing to a reduction in the viscosity, preferred examples thereof include methyl acetate, ethyl acetate, n-propyl acetate, n-butyl acetate, methyl propionate, ethyl propionate, n-propyl propionate, isopropyl propionate, methyl butyrate, and ethyl butyrate.

Also, a fluorinated acyclic carboxylate may also suitably be used. Preferred examples of the fluorine-containing ester include fluorinated acyclic carboxylates represented by the following formula (H):

$$Rf^{10}COORf^{11} \qquad (H)$$

(wherein $Rf^{10}$ is a C1-C2 fluorinated alkyl group; and $Rf^{11}$ is a C1-C4 fluorinated alkyl group) because they have high flame retardance, good compatibility with other solvents, and good oxidation resistance.

Examples of the group for $Rf^{10}$ include $CF_3$—, $CF_3CF_2$—, $HCF_2CF_2$—, $HCF_2$—, $CH_3CF_2$—, and $CF_3CH_2$—. In order to achieve good rate characteristics, $CF_3$— and $CF_3CF_2$— are particularly preferred.

Examples of the group for $Rf^{11}$ include —$CF_3$, —$CF_2CF_3$, —$CH(CF_3)_2$, —$CH_2CF_3$, —$CH_2CH_2CF_3$, —$CH_2CF_2CFHCF_3$, —$CH_2C_2F_5$, —$CH_2CF_2CF_2H$, —$CH_2CH_2C_2F_5$, —$CH_2CF_2CF_3$, and —$CH_2CF_2CF_2CF_3$. In order to achieve good compatibility with other solvents, —$CH_2CF_3$, —$CH(CF_3)_2$, —$CH_2C_2F_5$, and —$CH_2CF_2CF_2H$ are particularly preferred.

Specifically, for example, the fluorinated acyclic carboxylate may include one or two or more of $CF_3C(=O)OCH_2CF_3$, $CF_3C(=O)OCH_2CH_2CF_3$, $CF_3C(=O)OCH_2C_2F_5$, $CF_3C(=O)OCH_2CF_2CF_2H$, and $CF_3C(=O)OCH(CF_3)_2$. In order to achieve good compatibility with other solvents and good rate characteristics, $CF_3C(=O)OCH_2C_2F_5$, $CF_3C(=O)OCH_2CF_2CF_2H$, $CF_3C(=O)OCH_2CF_3$, and $CF_3C(=O)OCH(CF_3)_2$ are particularly preferred.

The ether compound is preferably a C3-C10 acyclic ether or a C3-C6 cyclic ether.

Examples of the C3-C10 acyclic ether include diethyl ether, di-n-butyl ether, dimethoxy methane, methoxy ethoxy methane, diethoxy methane, dimethoxy ethane, methoxy ethoxy ethane, diethoxy ethane, ethylene glycol di-n-propyl ether, ethylene glycol di-n-butyl ether, and diethylene glycol dimethyl ether.

The ether compound may suitably be a fluorinated ether.

One example of the fluorinated ether is a fluorinated ether (I) represented by the following formula (I):

$$Rf^{13}-O-Rf^{14} \qquad (I)$$

(wherein $Rf^{13}$ and $Rf^{14}$ are the same as or different from each other, and are each a C1-C10 alkyl group or a C1-C10 fluorinated alkyl group; and at least one of $Rf^{13}$ and $Rf^{14}$ is a fluorinated alkyl group). Containing the fluorinated ether (I) can improve the flame retardance of the electrolyte solution, as well as improve the stability and safety at high temperature under high voltage.

In the formula (I), at least one of $Rf^{13}$ and $Rf^{14}$ has only to be a C1-C10 fluorinated alkyl group. In order to further improve the flame retardance and the stability and safety at high temperature under high voltage of the electrolyte solution, both $Rf^{13}$ and $Rf^{14}$ are preferably a C1-C10 fluorinated alkyl group. In this case, $Rf^{13}$ and $Rf^{14}$ may be the same as or different from each other.

Preferably, $Rf^{13}$ and $Rf^{14}$ are the same as or different from each other, and $Rf^{13}$ is a C3-C6 fluorinated alkyl group and $Rf^{14}$ is a C2-C6 fluorinated alkyl group.

If the sum of the carbon numbers of $Rf^{13}$ and $Rf^{14}$ is too small, the fluorinated ether may have too low a boiling point. Too large a carbon number of $Rf^{13}$ or $Rf^{14}$ may cause low solubility of the electrolyte salt, which may cause a bad influence on the compatibility with other solvent, and the viscosity may be high so that the rate characteristics (viscousness) may be poor. In order to achieve excellent rate characteristics and boiling point, advantageously, the carbon number of $Rf^{13}$ is 3 or 4 and the carbon number of $Rf^{14}$ is 2 or 3.

The fluorinated ether (I) preferably has a fluorine content of 40 to 75 mass %. The fluorinated ether (I) having a fluorine content within this range may lead to particularly excellent balance between the flame retardance and the compatibility. The above range is also preferred for good oxidation resistance and safety.

The lower limit of the fluorine content is more preferably 45 mass %, still more preferably 50 mass %, particularly preferably 55 mass %. The upper limit thereof is more preferably 70 mass %, still more preferably 66 mass %.

The fluorine content of the fluorinated ether (I) is a value calculated by:

$$\{(\text{number of fluorine atoms} \times 19)/(\text{molecular weight of fluorinated ether (I)})\} \times 100 (\%)$$

based on the structural formula of the fluorinated ether (I).

Examples of the group for $Rf^{13}$ include $CF_3CF_2CH_2$—, $CF_3CFHCF_2$—, $HCF_2CF_2CF_2$—, $HCF_2CF_2CH_2$—, $CF_3CF_2CH_2CH_2$—, $CF_3CFHCF_2CH_2$—, $HCF_2CF_2CF_2CF_2$—, $HCF_2CF_2CF_2CH_2$—, $HCF_2CF_2CH_2CH_2$—, and $HCF_2CF(CF_3)CH_2$—. Examples of the group for $Rf^{14}$ include —$CH_2CF_2CF_3$, —CF$_2$CFHCF$_3$, —CF$_2$CF$_2$CF$_2$H, —CH$_2$CF$_2$CF$_2$H, —CH$_2$CH$_2$CF$_2$CF$_3$, —CH$_2$CF$_2$CFHCF$_3$, —CF$_2$CF$_2$CF$_2$CF$_2$H, —CH$_2$CF$_2$CF$_2$CF$_2$H, —CH$_2$CH$_2$CF$_2$CF$_2$H, —CH$_2$CF(CF$_3$)CF$_2$H, —CF$_2$CF$_2$H, —CH$_2$CF$_2$H, and —CF$_2$CH$_3$.

Specific examples of the fluorinated ether (I) include HCF$_2$CF$_2$CH$_2$OCF$_2$CF$_2$H, CF$_3$CF$_2$CH$_2$OCF$_2$CF$_2$H, HCF$_2$CF$_2$CH$_2$OCF$_2$CFHCF$_3$, CF$_3$CF$_2$CH$_2$OCF$_2$CFHCF$_3$, C$_6$F$_{13}$OCH$_3$, C$_6$F$_{13}$OC$_2$H$_5$, CsF$_{17}$OCH$_3$, CsF$_{17}$OC$_2$H$_5$, CF$_3$CFHCF$_2$CH(CH$_3$)OCF$_2$CFHCF$_3$, HCF$_2$CF$_2$OCH(C$_2$H$_5$)$_2$, HCF$_2$CF$_2$OC$_4$H$_9$, HCF$_2$CF$_2$OCH$_2$CH(C$_2$H$_5$)$_2$, and HCF$_2$CF$_2$OCH$_2$CH(CH$_3$)$_2$.

In particular, those having HCF$_2$— or CF$_3$CFH— at one end or both ends can provide a fluorinated ether (I) having excellent polarizability and a high boiling point. The boiling point of the fluorinated ether (I) is preferably 67° C. to 120° C. It is more preferably 80° C. or higher, still more preferably 90° C. or higher.

Such a fluorinated ether (I) may include one or two or more of CF$_3$CH$_2$OCF$_2$CFHCF$_3$, CF$_3$CF$_2$CH$_2$OCF$_2$CFHCF$_3$, HCF$_2$CF$_2$CH$_2$OCF$_2$CFHCF$_3$, HCF$_2$CF$_2$CH$_2$OCH$_2$CF$_2$CF$_2$H, CF$_3$CFHCF$_2$CH$_2$OCF$_2$CFHCF$_3$, HCF$_2$CF$_2$CH$_2$OCF$_2$CF$_2$H, and CF$_3$CF$_2$CH$_2$OCF$_2$CF$_2$H, for example.

In order to advantageously achieve a high boiling point, good compatibility with other solvents, and good solubility of the electrolyte salt, the fluorinated ether (I) is preferably at least one selected from the group consisting of HCF$_2$CF$_2$CH$_2$OCF$_2$CFHCF$_3$ (boiling point: 106° C.), CF$_3$CF$_2$CH$_2$OCF$_2$CFHCF$_3$ (boiling point: 82° C.), HCF$_2$CF$_2$CH$_2$OCF$_2$CF$_2$H (boiling point: 92° C.), and CF$_3$CF$_2$CH$_2$OCF$_2$CF$_2$H (boiling point: 68° C.), more preferably at least one selected from the group consisting of HCF$_2$CF$_2$CH$_2$OCF$_2$CFHCF$_3$ (boiling point: 106° C.) and HCF$_2$CF$_2$CH$_2$OCF$_2$CF$_2$H (boiling point: 92° C.).

Examples of the C3-C6 cyclic ether include 1,3-dioxane, 2-methyl-1,3-dioxane, 4-methyl-1,3-dioxane, 1,4-dioxane, and fluorinated compounds thereof. Preferred are dimethoxy methane, diethoxy methane, ethoxy methoxy methane, ethylene glycol n-propyl ether, ethylene glycol di-n-butyl ether, and diethylene glycol dimethyl ether because they have a high ability to solvate with lithium ions and improve the degree of ion dissociation. Particularly preferred are dimethoxy methane, diethoxy methane, and ethoxy methoxy methane because they have low viscosity and give a high ion conductivity.

Examples of the nitrogen-containing compound include nitrile, fluorine-containing nitrile, carboxylic acid amide, fluorine-containing carboxylic acid amide, sulfonic acid amide, and fluorine-containing sulfonic acid amide. Also, 1-methyl-2-pyrrolidinone, 1-methyl-2-piperidone, 3-methyl-2-oxazolidinone, 1,3-dimethyl-2-imidazolidinone, and N-methylsuccinimide may be used.

Examples of the boron-containing compound include borate esters such as trimethyl borate and triethyl borate, boric acid ethers, and alkyl borates.

Examples of the organic silicon-containing compound include (CH$_3$)$_4$—Si and (CH$_3$)$_3$—Si—Si(CH$_3$)$_3$.

Examples of the fireproof agent (flame retardant) include organophosphates and phosphazene-based compounds. Examples of the organophosphates include fluoroalkyl phosphates, non-fluoroalkyl phosphates, and aryl phosphates. Particularly preferred are fluoroalkyl phosphates because they can show a flame retardant effect even at a small amount.

Specific examples of the fluoroalkyl phosphates include fluorodialkyl phosphates disclosed in JP H11-233141 A, alkyl phosphates disclosed in JP H11-283669 A, and fluorotrialkyl phosphates.

Preferred as the fireproof agent (flame retardant) are (CH$_3$O)$_3$P═O and (CF$_3$CH$_2$O)$_3$P═O, for example.

The surfactant may be any of cationic surfactants, anionic surfactants, nonionic surfactants, and amphoteric surfactants. In order to achieve good cycle characteristics and rate characteristics, the surfactant is preferably one containing a fluorine atom.

Preferred examples of such a surfactant containing a fluorine atom include fluorine-containing carboxylic acid salts represented by the following formula (J):

$$Rf^{15}COO\text{-}M^+ \qquad (J)$$

(wherein Rf$^{15}$ is a C3-C10 fluorine-containing alkyl group which may optionally contain an ether bond; M$^+$ is Li$^+$, Na$^+$, K$^+$, or NHR'$_3^+$ (where R's are the same as or different from each other, and are each H or a C1-C3 alkyl group)), and fluorine-containing sulfonic acid salts represented by the following formula (K):

$$Rf^{16}SO_3\text{-}M^+ \qquad (K)$$

(wherein Rf$^{16}$ is a C3-C10 fluorine-containing alkyl group which may optionally contain an ether bond; M$^+$ is Li$^+$, Na$^+$, K$^+$, or NHR'$_3^+$ (where R's are the same as or different from each other, and are each H or a C1-C3 alkyl group)).

In order to reduce the surface tension of the electrolyte solution without impairing the charge and discharge cycle characteristics, the amount of the surfactant is preferably 0.01 to 2 mass % in the electrolyte solution.

Examples of the additive for increasing the permittivity include sulfolane, methyl sulfolane, γ-butyrolactone, γ-valerolactone, acetonitrile, and propionitrile.

Examples of the improver for cycle characteristics and rate characteristics include methyl acetate, ethyl acetate, tetrahydrofuran, and 1,4-dioxane.

In order to suppress burst or combustion of batteries in case of overcharge, for example, the overcharge inhibitor is preferably an overcharge inhibitor having an aromatic ring. Examples of the overcharge inhibitor having an aromatic ring include aromatic compounds such as cyclohexyl benzene, biphenyl, alkyl biphenyl, terphenyl, partially hydrogenated terphenyl, t-butyl benzene, t-amyl benzene, diphenyl ether, benzofuran, dibenzofuran, dichloroaniline, and toluene; fluorinated aromatic compounds such as hexafluorobenzene, fluorobenzene, 2-fluorobiphenyl, o-cyclohexyl fluorobenzene, and p-cyclohexyl fluorobenzene; and fluoroanisole compounds such as 2,4-difluoroanisole, 2,5-difluoroanisole, 2,6-difluoroanisole, and 3,5-difluoroanisole. Preferred are aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran. These compounds may be used alone or in combination of two or more. In the case of combination use of two or more compounds, in order to achieve good balance between the overcharge inhibiting characteristics and the high-temperature storage characteristics, preferred are a combination of cyclohexyl benzene and t-butyl benzene or t-amyl benzene, and a combination of at least one oxygen-free aromatic compound selected from biphenyl, alkyl biphenyl, terphenyl, partially hydrogenated terphenyl, cyclohexyl benzene, t-butyl benzene, t-amyl benzene, and the like, and at least one oxygen-containing aromatic compound selected from diphenyl ether, dibenzofuran, and the like.

In order to prevent burst or combustion of batteries in case of overcharge, for example, the amount of the overcharge inhibitor is preferably 0.1 to 5 mass % in the electrolyte solution.

The electrolyte solution may further contain other known assistants to the extent that the performance of the electrolyte solution is not impaired. Examples of such known assistants include carbonate compounds such as erythrinan carbonate, spiro-bis-dimethylene carbonate, and methoxy ethyl-methyl carbonate; carboxylic anhydrides such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenylsuccinic anhydride; spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, methyl fluorosulfonate, ethyl fluorosulfonate, methyl methanesulfonate, ethyl methanesulfonate, busulfan, sulfolene, diphenyl sulfone, N,N-dimethyl methane sulfone amide, N,N-diethyl methane sulfone amide, and like other chain sulfones, fluorine-containing chain sulfones, chain sulfonates, fluorine-containing chain sulfonates, cyclic sulfones, fluorine-containing cyclic sulfones, halides of sulfonic acid, and halides of fluorine-containing sulfonic acid; and fluoroaromatic compounds of hydrocarbon compounds, including heptane, octane, nonane, decane, and cycloheptane. These compounds may be used alone or in combination of two or more. These assistants can improve the capacity retention characteristics and the cycle characteristics after high-temperature storage.

The electrolyte solution may be combined with a polymer material and thereby formed into a gel-like (plasticized), gel electrolyte solution.

Examples of such a polymer material include conventionally known polyethylene oxide and polypropylene oxide, modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); and complexes of any of these fluororesins and any hydrocarbon resin (see JP H11-35765 A, JP H11-86630 A). In particular, polyvinylidene fluoride or a vinylidene fluoride-hexafluoropropylene copolymer is preferably used as a polymer material for gel electrolytes.

The electrolyte solution may also contain an ion conductive compound disclosed in Japanese Patent Application No. 2004-301934.

This ion conductive compound is an amorphous fluoropolyether compound having a fluorine-containing group at a side chain and is represented by the following formula (1-1):

A-(D)-B    (1-1)

wherein D is represented by the following formula (2-1a):

[wherein D1 is an ether unit having a fluoroether group at a side chain and is represented by the following formula (2a):

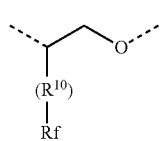

(wherein Rf is a fluoroether group which may optionally contain a cross-linkable functional group; and $R^{10}$ is a group or a bond that links Rf and the main chain);

FAE is an ether unit having a fluorinated alkyl group at a side chain and is represented by the following formula (2b):

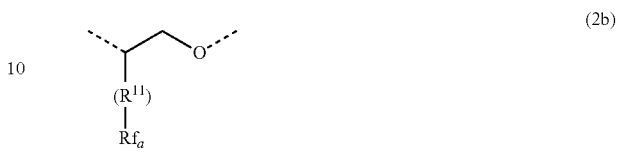

(wherein Rfa is a hydrogen atom or a fluorinated alkyl group which may optionally contain a cross-linkable functional group; and $R^{11}$ is a group or a bond that links Rfa and the main chain);

AE is an ether unit represented by the following formula (2c):

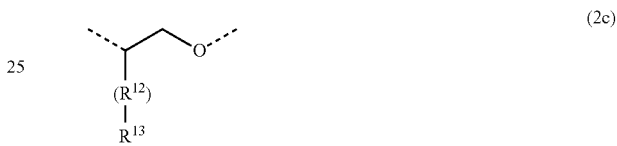

(wherein $R^{13}$ is a hydrogen atom, an alkyl group which may optionally contain a cross-linkable functional group, an aliphatic cyclic hydrocarbon group which may optionally contain a cross-linkable functional group, or an aromatic hydrocarbon group which may optionally contain a cross-linkable functional group; and $R^{12}$ is a group or a bond that links $R^{13}$ and the main chain);

Y is a unit having at least one selected from the following formulas (2d-1) to (2d-3):

n is an integer of 0 to 200;
m is an integer of 0 to 200;
p is an integer of 0 to 10000;
q is an integer of 1 to 100;
n+m is not 0; and
the bonding order of D1, FAE, AE, and Y is not specified]; and A and B are the same as or different from each other, and are each a hydrogen atom, an alkyl group which may optionally contain a fluorine atom and/or a cross-linkable functional group, a phenyl group which may optionally contain a fluorine atom and/or a cross-linkable functional group, a —COOH group, —OR (where R is a hydrogen atom or an alkyl group which may optionally contain a fluorine atom and/or a cross-linkable functional group), an ester group, or a carbonate group (if an end of D is an oxygen atom, A and B each are none of a —COOH group, —OR, an ester group, and a carbonate group).

The electrolyte solution may further contain any other additives, if necessary. Examples of such other additives include metal oxides and glass.

The electrolyte solution may be prepared by any method using the aforementioned components.

The electrolyte solution can be suitably applied to electrochemical devices such as secondary batteries.

Examples of the electrochemical devices include lithium ion secondary batteries, capacitors (electric double-layer capacitors), radical batteries, solar cells (in particular, dye-sensitized solar cells), fuel cells, various electrochemical sensors, electrochromic elements, electrochemical switching elements, aluminum electrolytic capacitors, and tantalum electrolytic capacitors. Preferred are lithium ion secondary batteries and electric double-layer capacitors.

In the following, a lithium ion secondary battery is described as an example of the electrochemical devices or secondary batteries.

The lithium ion secondary battery includes a positive electrode, a negative electrode, and the aforementioned electrolyte solution.

<Positive Electrode>

The positive electrode is formed from a positive electrode mixture containing a positive electrode active material, which is a material of the positive electrode, and a current collector.

The positive electrode active material may be any material that can electrochemically occlude and release lithium ions. For example, a substance containing lithium and at least one transition metal is preferred. Specific examples thereof include lithium-containing transition metal complex oxides and lithium-containing transition metal phosphoric acid compounds. In particular, the positive electrode active material is preferably a lithium-containing transition metal complex oxide that generates a high voltage.

Examples of the lithium-containing transition metal complex oxides include lithium-manganese spinel complex oxides represented by the formula (L): $Li_aMn_{2-b}M^1{}_bO_4$ (wherein $0.9 \leq a$; $0 \leq b \leq 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge),
lithium-nickel complex oxides represented by the formula (M): $LiNi_{1-c}M^2{}_cO_2$ (wherein $0 \leq c \leq 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge), and
lithium-cobalt complex oxides represented by the formula (N): $LiCo_{1-d}M^3{}_dO_2$ (wherein $0 \leq d \leq 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge).

In order to provide a high-power lithium ion secondary battery having a high energy density, preferred is $LiCoO_2$, $LiMnO_2$, $LiNiO_2$, $LiMn_2O_4$, $LiNi_{0.8}Co_{0.15}Al_{0.5}O_2$, or $LiNi_{1/3}Co_{1/3}Mn_{1/3}O_2$.

Examples of other positive electrode active materials include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

In order to improve the continuous charge characteristics, the positive electrode active material preferably contains lithium phosphate. The use of lithium phosphate may be achieved in any manner, and the positive electrode active material and lithium phosphate are preferably used in a mixed state. The lower limit of the amount of lithium phosphate in the sum of the amounts of the positive electrode active material and the lithium phosphate is preferably 0.1 mass % or more, more preferably 0.3 mass % or more, still more preferably 0.5 mass % or more, whereas the upper limit thereof is preferably 10 mass % or less, more preferably 8 mass % or less, still more preferably 5 mass % or less.

To the surface of the positive electrode active material may be attached a substance having a composition different from the positive electrode active material. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, magnesium carbonate; and carbon.

Such a substance may be attached to the surface of the positive electrode active material by, for example, a method of dissolving or suspending the substance in a solvent, impregnating the positive electrode active material with the solution or suspension, and drying the impregnated material; a method of dissolving or suspending a precursor of the substance in a solvent, impregnating the positive electrode active material with the solution or suspension, and reacting the material and the precursor by heating; or a method of adding the substance to a precursor of the positive electrode active material and simultaneously sintering the materials. In the case of attaching carbon, a carbonaceous material in the form of activated carbon, for example, may be mechanically attached to the surface afterward.

The lower limit of the amount (in terms of mass) of the substance attached to the surface relative to the amount of the positive electrode active material is preferably 0.1 ppm or more, more preferably 1 ppm or more, still more preferably 10 ppm or more, whereas the upper limit thereof is preferably 20% or less, more preferably 10% or less, still more preferably 5% or less. The substance attached to the surface can suppress the oxidation of the electrolyte solution on the surface of the positive electrode active material, improving the battery life. Too small an amount thereof may fail to sufficiently provide the effect. Too large an amount thereof may hinder the entrance and exit of lithium ions, possibly increasing the resistance.

Particles of the positive electrode active material may have any conventionally used shape, such as an agglomerative shape, a polyhedral shape, a spherical shape, an ellipsoidal shape, a plate shape, a needle shape, or a pillar shape. The primary particles may agglomerate to form secondary particles.

The positive electrode active material has a tap density of preferably 0.5 g/cm$^3$ or higher, more preferably 0.8 g/cm$^3$ or higher, still more preferably 1.0 g/cm$^3$ or higher. If the tap density of the positive electrode active material is below the lower limit, an increased amount of a dispersion medium is required, as well as increased amounts of a conductive material and a binder are required in formation of a positive electrode active material layer. Thus, the filling rate of the positive electrode active material into the positive electrode active material layer may be limited and the battery capacity may be limited. With a complex oxide powder having a high tap density, a positive electrode active material layer with a high density can be formed. The tap density is preferably as high as possible and has no upper limit, in general. Still, if the tap density is too high, diffusion of lithium ions in the positive electrode active material layer with the electrolyte solution serving as a diffusion medium may function as a rate-determining step, so that the load characteristics may be easily impaired. Thus, the upper limit of the tap density is preferably 4.0 g/cm$^3$ or lower, more preferably 3.7 g/cm$^3$ or lower, still more preferably 3.5 g/cm$^3$ or lower.

The tap density is determined as a powder filling density (tap density) g/cm$^3$ when 5 to 10 g of the positive electrode active material powder is filled into a 10-ml glass graduated cylinder and the cylinder is tapped 200 times with a stroke of about 20 mm.

The particles of the positive electrode active material have a median size d50 (if the primary particles agglomerate to form secondary particles, the secondary particle size) of preferably 0.3 μm or greater, more preferably 0.5 μm or greater, still more preferably 0.8 μm or greater, most preferably 1.0 μm or greater, while preferably 30 μm or smaller, more preferably 27 μm or smaller, still more preferably 25 μm or smaller, most preferably 22 μm or smaller. If the median size is below the lower limit, products with a high tap density may not be obtained. If the median size exceeds the upper limit, diffusion of lithium in the particles may take a long time, so that the battery performance may be poor or streaks may be formed in formation of positive electrodes for batteries, i.e., when the active material and components such as a conductive material and a binder are formed into slurry by adding a solvent and the slurry is applied in the form of a film, for example. Mixing two or more positive electrode active materials having different median sizes d50 leads to further improved filling in formation of positive electrodes.

The median size d50 is determined using a known laser diffraction/scattering particle size distribution analyzer. In the case of using LA-920 (Horiba, Ltd.) as the particle size distribution analyzer, the dispersion medium used in the measurement is a 0.1 mass % sodium hexametaphosphate aqueous solution and the measurement refractive index is set to 1.24 after 5-minute ultrasonic dispersion.

If the primary particles agglomerate to form secondary particles, the average primary particle size of the positive electrode active material is preferably 0.05 μm or greater, more preferably 0.1 μm or greater, still more preferably 0.2 μm or greater. The upper limit thereof is preferably 5 μm or smaller, more preferably 4 μm or smaller, still more preferably 3 μm or smaller, most preferably 2 μm or smaller. If the average primary particle size exceeds the upper limit, spherical secondary particles are difficult to form, which may have a bad influence on the powder filling or may cause a great reduction in the specific surface area. Thus, the battery performance such as output characteristics is more likely to be impaired. In contrast, if the average primary particle size is below the lower limit, the crystals usually do not sufficiently grow. Thus, charge and discharge may be poorly reversible, for example.

The primary particle size is measured by scanning electron microscopic (SEM) observation. Specifically, the primary particle size is determined as follows. First, a photograph at a magnification of 10000× is taken. Any 50 primary particles are selected and the maximum length between the left and right boundary lines of each primary particle is measured along the horizontal line. Then, the average value of the maximum lengths is calculated, which is defined as the primary particle size.

The positive electrode active material has a BET specific surface area of preferably 0.1 m$^2$/g or larger, more preferably 0.2 m$^2$/g or larger, still more preferably 0.3 m$^2$/g or larger, while preferably 50 m$^2$/g or smaller, more preferably 40 m$^2$/g or smaller, still more preferably 30 m$^2$/g or smaller. If the BET specific surface area is smaller than the above range, the battery performance may be easily impaired. If it is larger than the above range, the tap density is less likely to be high and formation of the positive electrode active material layer may involve a difficulty in applying the material.

The BET specific surface area is defined by a value determined by single point BET nitrogen adsorption utilizing a gas flow method using a surface area analyzer (e.g., fully automatic surface area measurement device, Ohkura Riken Co., Ltd.), a sample pre-dried in the stream of nitrogen at 150° C. for 30 minutes, and a nitrogen-helium gas mixture with the nitrogen pressure relative to the atmospheric pressure being accurately adjusted to 0.3.

When the lithium ion secondary battery is used as a large-size lithium ion secondary battery for hybrid vehicles or distributed generation, it is required to achieve a high output. Thus, the particles of the positive electrode active material preferably mainly include secondary particles.

The particles of the positive electrode active material preferably include 0.5 to 7.0 vol % of fine particles having an average secondary particle size of 40 μm or smaller and having an average primary particle size of 1 μm or smaller. Containing fine particles having an average primary particle size of 1 μm or smaller leads to an increase in the contact area with the electrolyte solution and more rapid diffusion of lithium ions between the electrode and the electrolyte solution. As a result, the output performance of the battery can be improved.

The positive electrode active material can be produced by any usual method of producing inorganic compounds. In particular, a spherical or ellipsoidal active material can be produced by various methods. For example, a material substance of transition metal is dissolved or crushed and dispersed in a solvent such as water, and the pH of the solution or dispersion is adjusted under stirring to form a spherical precursor. The precursor is recovered and, if necessary, dried. Then, a Li source such as LiOH, $Li_2CO_3$, or $LiNO_3$ is added thereto and the mixture is sintered at high temperature, thereby providing an active material.

In order to produce a positive electrode, the aforementioned positive electrode active materials may be used alone or in any combination with one or more having different compositions at any ratio. Preferred examples of the combination in this case include a combination of $LiCoO_2$ and $LiMn_2O_4$ in which part of Mn may optionally be replaced by a different transition metal (e.g., $LiNi_{0.33}Co_{0.33}Mn_{0.33}O_2$), and a combination with $LiCoO_2$ in which part of Co may optionally be replaced by a different transition metal.

In order to achieve a high battery capacity, the amount of the positive electrode active material is preferably 50 to 99 mass %, more preferably 80 to 99 mass %, of the positive electrode mixture. The amount of the positive electrode active material in the positive electrode active material layer is preferably 80 mass % or more, more preferably 82 mass % or more, particularly preferably 84 mass % or more. The amount thereof is preferably 99 mass % or less, more preferably 98 mass % or less. Too small an amount of the positive electrode active material in the positive electrode active material layer may lead to an insufficient electric capacity. In contrast, too large an amount thereof may lead to an insufficient strength of the resulting positive electrode.

The positive electrode mixture preferably further contains a binder, a thickening agent, and a conductive material.

The binder may be any material that is safe against a solvent to be used in production of the electrode and against the electrolyte solution. Examples thereof include polyvinylidene fluoride, polytetrafluoroethylene, polyethylene, polypropylene, styrene-butadiene rubber (SBR), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, acrylonitrile-butadiene rubber (NBR), fluororubber, ethylene-propylene rubber, styrene-butadiene-styrene block copolymers or hydrogenated products thereof, ethylene-propylene-diene terpolymers (EPDM), styrene-ethylene-butadiene-ethylene copolymers, styrene-isoprene-styrene block copolymers or hydrogenated products thereof, syndiotactic-1,2-polybutadiene, polyvinyl acetate, ethylene-vinyl acetate copolymers, propylene-α-olefin copolymers, fluorinated polyvinylidene fluoride, tetrafluoroethylene-ethylene copolymers, and polymer compositions having an ion conductivity of alkali metal ions (especially, lithium ions). These agents may be used alone or in any combination of two or more at any ratio.

The amount of the binder, which is expressed as the proportion of the binder in the positive electrode active material layer, is usually 0.1 mass % or more, preferably 1 mass % or more, more preferably 1.5 mass % or more, while usually 80 mass % or less, preferably 60 mass % or less, still more preferably 40 mass % or less, most preferably 10 mass % or less. Too low a proportion of the binder may fail to sufficiently hold the positive electrode active material so that the resulting positive electrode may have an insufficient mechanical strength, resulting in impaired battery performance such as cycle characteristics. In contrast, too high a proportion thereof may lead to a reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1 mass % or more, preferably 0.2 mass % or more, more preferably 0.3 mass % or more, while usually 5 mass % or less, preferably 3 mass % or less, more preferably 2 mass % or less. If the proportion thereof is below this range, easiness of application may be significantly impaired. If the proportion exceeds this range, the proportion of the active material in the positive electrode active material layer is low, so that the capacity of the battery may be low or the resistance between the positive electrode active materials may be high.

The conductive material may be any known conductive material. Specific examples thereof include metal materials such as copper and nickel, and carbon materials such as graphite (e.g., natural graphite, artificial graphite), carbon black (e.g., acetylene black), and amorphous carbon (e.g., needle coke). These materials may be used alone or in any combination of two or more at any ratio. The conductive material is used such that the amount thereof in the positive electrode active material layer is usually 0.01 mass % or more, preferably 0.1 mass % or more, more preferably 1 mass % or more, while usually 50 mass % or less, preferably 30 mass % or less, more preferably 15 mass % or less. If the amount thereof is below this range, the conductivity may be insufficient. In contrast, if the amount is above this range, the battery capacity may be low.

The solvent for forming slurry may be any solvent that can dissolve or disperse therein the positive electrode active material, the conductive material, and the binder, as well as a thickening agent that is used as necessary. The solvent may be either an aqueous solvent or an organic solvent. Examples of the aqueous medium include water and solvent mixtures of an alcohol and water. Examples of the organic medium include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropylamine; ethers such as diethyl ether, propylene oxide, and tetrahydrofuran (THF); amides such as N-methylpyrrolidone (NMP), dimethylformamide, and dimethyl acetamide; and aprotic polar solvents such as hexamethyl phosphramide and dimethyl sulfoxide.

Examples of the material of the current collector for positive electrodes include metal materials such as aluminum, titanium, tantalum, stainless steel, and nickel, and any alloy thereof; and any carbon material such as carbon cloth and carbon paper. Preferred is a metal material, especially aluminum or an alloy thereof.

In the case of a metal material, the current collector may be in the form of metal foil, metal cylinder, metal coil, metal plate, metal film, expanded metal, punched metal, metal foam, or the like. In the case of a carbon material, it may be in the form of carbon plate, carbon film, carbon cylinder, or the like. Preferred among these is a metal film. The film may be in the form of mesh, as appropriate. The film may have any thickness, and the thickness is usually 1 μm or greater, preferably 3 μm or greater, more preferably 5 μm or greater, while usually 1 mm or smaller, preferably 100 μm or smaller, more preferably 50 μm or smaller. If the film is thinner than this range, it may have an insufficient strength as a current collector. In contrast, if the film is thicker than this range, it may have poor handleability.

In order to reduce the electronic contact resistance between the current collector and the positive electrode active material layer, the current collector also preferably has a conductive aid applied on the surface thereof. Examples of the conductive aid include carbon and noble metals such as gold, platinum, and silver.

The ratio between the thicknesses of the current collector and the positive electrode active material layer may be any value, and the ratio ((thickness of positive electrode active material layer on one side immediately before injection of electrolyte solution)/(thickness of current collector)) is preferably 20 or lower, more preferably 15 or lower, most preferably 10 or lower. The ratio is also preferably 0.5 or higher, more preferably 0.8 or higher, most preferably 1 or higher. If the ratio exceeds this range, the current collector may generate heat due to Joule heating during high-current-density charge and discharge. If the ratio is below this range, the ratio by volume of the current collector to the positive electrode active material is so high that the capacity of the battery may be low.

The positive electrode may be produced by a usual method. One example of the production method is a method in which the positive electrode active material is mixed with the aforementioned binder, thickening agent, conductive material, solvent, and other components to form a slurry-like positive electrode mixture, and then this mixture is applied to a current collector, dried, and pressed so as to be densified.

The densification may be achieved using a manual press or a roller press, for example. The density of the positive electrode active material layer is preferably 1.5 g/cm$^3$ or higher, more preferably 2 g/cm$^3$ or higher, still more preferably 2.2 g/cm$^3$ or higher, while preferably 5 g/cm$^3$ or lower, more preferably 4.5 g/cm$^3$ or lower, still more preferably 4 g/cm³ or lower. If the density is above this range, the permeability of the electrolyte solution toward the vicinity of the interface between the current collector and the active material may be low, in particular, the charge and discharge characteristics at high current density may be impaired, so that a high output may not be achieved. If the density is below this range, the conductivity between the active materials may be low and the resistance of the battery may increase, so that a high output may not be achieved.

In the case of using the electrolyte solution, in order to improve the stability at high output and high temperature, the area of the positive electrode active material layer is preferably large relative to the outer surface area of an external case of the battery. Specifically, the sum of the areas of the positive electrodes is preferably 15 times or more, more preferably 40 times or more, greater than the surface area of the external case of the secondary battery. For closed, square-shaped cases, the outer surface area of an external case of the battery herein refers to the total area calculated from the dimension of length, width, and thickness of the case portion into which a power-generating element is filled except for the protruding portions of the terminals. For closed, cylinder-shaped cases, the outer surface area of an external case of the battery herein refers to a geometric surface area of an approximated cylinder of the case portion into which a power-generating element is filled except for the protruding portion of the terminals. The sum of the areas of the positive electrodes herein refers to a geometric surface area of a positive electrode mixture layer opposite to a mixture layer including the negative electrode active material. For structures including a current collector foil and positive electrode mixture layers on both sides of the current collector, the sum of the areas of the positive electrodes is the sum of the areas calculated on the respective sides.

The positive electrode plate may have any thickness. In order to achieve a high capacity and a high output, the lower limit of the thickness of the mixture layer on one side of the current collector excluding the thickness of the base metal foil is preferably 10 μm or greater, more preferably 20 μm or greater, while preferably 500 μm or smaller, more preferably 450 μm or smaller.

To the surface of the positive electrode plate may be attached a substance having a different composition. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

<Negative Electrode>

The negative electrode is formed from a negative electrode mixture including a negative electrode active material, and a current collector.

Examples of the negative electrode active material include carbonaceous material that can occlude and release lithium such as pyrolysates of organic matter under various pyrolysis conditions, artificial graphite, and natural graphite; metal oxide material that can occlude and release lithium such as tin oxide and silicon oxide; lithium metals; various lithium alloys; and lithium-containing metal complex oxide material. Two or more of these negative electrode active materials may be used in a mixed state.

The carbonaceous material that can occlude and release lithium is preferably artificial graphite produced by high-temperature treatment of easily graphitizable pitch from various materials, purified natural graphite, or material obtained by surface-treating such graphite with pitch or other organic matter and then carbonizing the surface-treated graphite. In order to achieve a good balance between the initial irreversible capacity and the high-current-density charge and discharge characteristics, it is more preferably one selected from carbonaceous material obtained by one or more heat treatments at 400° C. to 3200° C. on natural graphite, artificial graphite, an artificial carbonaceous substance, or an artificial graphite substance; carbonaceous material which allows the negative electrode active material layer to include at least two or more carbonaceous matters having different crystallinities and/or to have an interface between the carbonaceous matters having the different crystallinities; and carbonaceous material which allows the negative electrode active material layer to have an interface between at least two or more carbonaceous matters having different orientations. These carbonaceous materials may be used alone or in any combination of two or more at any ratio.

Examples of the carbonaceous material obtained by one or more heat treatments at 400° C. to 3200° C. on an artificial carbonaceous substance or an artificial graphite substance include coal-based coke, petroleum-based coke, coal-based pitch, petroleum-based pitch, and those prepared by oxidizing these pitches; needle coke, pitch coke, and carbon material prepared by partially graphitizing these cokes; pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The metal material (excluding lithium-titanium complex oxides) to be used as the negative electrode active material may be any compound that can occlude and release lithium, and examples thereof include simple lithium, simple metals and alloys that constitute lithium alloys, and oxides, carbides, nitrides, silicides, sulfides, and phosphides thereof. The simple metals and alloys constituting lithium alloys are preferably materials containing any of metal and semi-metal elements in the Groups 13 and 14, more preferably simple metal of aluminum, silicon, and tin (hereinafter, referred to as "specific metal elements"), and alloys and compounds containing any of these atoms. These materials may be used alone or in combination of two or more at any ratio.

Examples of the negative electrode active material having at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of the compounds. Use of such a simple metal, alloy, or metal compound as the negative electrode active material can give a high capacity to batteries.

Examples thereof further include compounds in which any of the above composite compounds are complexly bonded with several elements such as simple metals, alloys, and nonmetal elements. Specifically, in the case of silicon or tin, for example, an alloy of this element and a metal that does not serve as a negative electrode can be used. In the case of tin, for example, a composite compound including a combination of 5 or 6 elements, including tin, a metal (excluding silicon) that serves as a negative electrode, a metal that does not serve as a negative electrode, and a nonmetal element, can be used.

Specific examples thereof include simple Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_6Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiOv$ (0<v≤2), LiSiO, simple tin, $SnSiO_3$, LiSnO, $Mg_2Sn$, and SnOw (0<w≤2).

Examples thereof further include composite materials of Si or Sn used as a first constitutional element, and second and third constitutional elements. The second constitutional element is at least one selected from cobalt, iron, magnesium, titanium, vanadium, chromium, manganese, nickel, copper, zinc, gallium, and zirconium, for example. The third constitutional element is at least one selected from boron, carbon, aluminum, and phosphorus, for example.

In order to achieve a high battery capacity and excellent battery characteristics, the metal material is preferably simple silicon or tin (which may contain trace impurities), SiOv (0<v≤2), SnOw (0<w≤2), a Si—Co—C composite material, a Si—Ni—C composite material, a Sn—Co—C composite material, or a Sn—Ni—C composite material.

The lithium-containing metal complex oxide material to be used as the negative electrode active material may be any material that can occlude and release lithium. In order to achieve good high-current-density charge and discharge characteristics, materials containing titanium and lithium are preferred, lithium-containing metal complex oxide materials containing titanium are more preferred, and complex oxides of lithium and titanium (hereinafter, abbreviated as "lithium titanium complex oxides") are still more preferred. In other words, use of a spinel-structured lithium titanium complex oxide contained in the negative electrode active material for electrolyte batteries is particularly preferred because such a compound markedly reduces the output resistance.

Preferred examples of the lithium titanium complex oxides include compounds represented by the following formula (O):

$$Li_xTi_yM_zO_4 \qquad (O)$$

wherein M is at least one element selected from the group consisting of Na, K, Co, Al, Fe, Ti, Mg, Cr, Ga, Cu, Zn, and Nb.

Particularly preferred compositions represented by the formula (O) are those satisfying one of the following:
(i) 1.2≤x≤1.4, 1.5≤y≤1.7, z=0
(ii) 0.9≤x≤1.1, 1.9≤y≤2.1, z=0
(iii) 0.7≤x≤0.9, 2.1≤y≤2.3, z=0
because the compound structure satisfying any of these compositions gives good balance of the battery performance.

Particularly preferred representative compositions of the compound are $Li_{4/3}Ti_{5/3}O_4$ corresponding to the composition (i), $Li_1Ti_2O_4$ corresponding to the composition (ii), and $Li_{4/5}Ti_{11/5}O_4$ corresponding to the composition (iii). Preferred examples of the structure satisfying Z≠0 include $Li_{4/3}Ti_{4/3}Al_{1/3}O_4$.

The negative electrode mixture preferably further contains a binder, a thickening agent, and a conductive material.

Examples of the binder include the same binders as those mentioned for the positive electrode. The proportion of the binder relative to the negative electrode active material is preferably 0.1 mass % or more, more preferably 0.5 mass % or more, particularly preferably 0.6 mass % or more, while preferably 20 mass % or less, more preferably 15 mass % or less, still more preferably 10 mass % or less, particularly preferably 8 mass % or less. If the proportion of the binder relative to the negative electrode active material exceeds the above range, a large amount of the binder may fail to contribute to the battery capacity, so that the battery capacity may be low. If the proportion is lower than the above range, the negative electrode may have a lowered strength.

In particular, in the case of using a rubbery polymer typified by SBR as a main component, the proportion of the binder relative to the negative electrode active material is usually 0.1 mass % or more, preferably 0.5 mass % or more, more preferably 0.6 mass % or more, while usually 5 mass % or less, preferably 3 mass % or less, more preferably 2 mass % or less. In the case of using a fluoropolymer typified by polyvinylidene fluoride as a main component, the proportion of the binder relative to the negative electrode active material is usually 1 mass % or more, preferably 2 mass % or more, more preferably 3 mass % or more, while usually 15 mass % or less, preferably 10 mass % or less, more preferably 8 mass % or less.

Examples of the thickening agent include the same thickening agents as those mentioned for the positive electrode. The proportion of the thickening agent relative to the negative electrode active material is usually 0.1 mass % or more, preferably 0.5 mass % or more, still more preferably 0.6 mass % or more, while usually 5 mass % or less, preferably 3 mass % or less, still more preferably 2 mass % or less. If the proportion of the thickening agent relative to the negative electrode active material is below this range, easiness of application may be significantly impaired. If the proportion thereof exceeds the above range, the proportion of the negative electrode active material in the negative electrode active material layer is low, so that the capacity of the battery may be low or the resistance between the negative electrode active materials may be high.

Examples of the conductive material of the negative electrode include metal materials such as copper and nickel; and carbon materials such as graphite and carbon black.

The solvent for forming slurry may be any solvent that can dissolve or disperse therein the negative electrode active material and the binder, as well as a thickening agent and a conductive material that are used as necessary. The slurry-forming solvent may be either an aqueous solvent or an organic solvent.

Examples of the aqueous solvent include water and alcohols. Examples of the organic solvent include N-methylpyrrolidone (NMP), dimethylformamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phosphramide, dimethyl sulfoxide, benzene, xylene, quinoline, pyridine, methyl naphthalene, and hexane.

Examples of the material of the current collector for negative electrodes include copper, nickel, and stainless steel. For easy processing of the material into a film and low cost, copper is preferred.

The current collector usually has a thickness of 1 μm or greater, preferably 5 μm or greater, while usually 100 μm or smaller, preferably 50 μm or smaller. Too thick a negative electrode current collector may cause an excessively low capacity of the whole battery, whereas too thin a current collector may be difficult to handle.

The negative electrode may be produced by a usual method. One example of the production method is a method in which the negative electrode material is mixed with the aforementioned binder, thickening agent, conductive material, solvent, and other components to form a slurry-like mixture, and then this mixture is applied to a current collector, dried, and pressed so as to be densified. In the case of using an alloyed material, a thin film layer containing the above negative electrode active material (negative electrode active material layer) can be produced by vapor deposition, sputtering, plating, or a like technique.

The electrode formed from the negative electrode active material may have any structure. The density of the negative electrode active material existing on the current collector is preferably 1 g·cm$^{-3}$ or higher, more preferably 1.2 g·cm$^{-3}$ or higher, particularly preferably 1.3 g·cm$^{-3}$ or higher, whereas the density thereof is preferably 2.2 g·cm$^{-3}$ or lower, more preferably 2.1 g·cm$^{-3}$ or lower, still more preferably 2.0 g·cm$^{-3}$ or lower, particularly preferably 1.9 g·cm$^{-3}$ or lower. If the density of the negative electrode active material existing on the current collector exceeds the above range, the particles of the negative electrode active material may be broken, the initial irreversible capacity may be high, and the permeability of the electrolyte solution toward the vicinity of the interface between the current collector and the negative electrode active material may be impaired, so that the high-current-density charge and discharge characteristics may be impaired. If the density thereof is below the above range, the conductivity between the negative electrode active materials may be impaired, the resistance of the battery may be high, and the capacity per unit volume may be low.

The thickness of the negative electrode plate is a design matter in accordance with the positive electrode plate to be used, and may be any value. The thickness of the mixture layer excluding the thickness of the base metal foil is usually 15 µm or greater, preferably 20 µm or greater, more preferably 30 µm or greater, while usually 300 µm or smaller, preferably 280 µm or smaller, more preferably 250 µm or smaller.

To the surface of the negative electrode plate may be attached a substance having a different composition. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

The lithium ion secondary battery preferably further includes a separator.

The separator may be formed from any known material and may have any known shape as long as the resulting separator is stable to the electrolyte solution and has excellent liquid-retaining ability. The separator is preferably in the form of a porous sheet or a nonwoven fabric which is formed from a material stable to the electrolyte solution, such as resin, glass fiber, or inorganic matter, and which has excellent liquid-retaining ability.

Examples of the material of a resin or glass-fiber separator include polyolefins such as polyethylene and polypropylene, aromatic polyamide, polytetrafluoroethylene, polyether sulfone, and glass filters. These materials may be used alone or in any combination of two or more at any ratio, for example, in the form of a polypropylene/polyethylene bilayer film or a polypropylene/polyethylene/polypropylene trilayer film. In order to achieve good permeability of the electrolyte solution and a good shut-down effect, the separator is particularly preferably a porous sheet or a nonwoven fabric formed from polyolefin such as polyethylene or polypropylene.

The separator may have any thickness, and the thickness is usually 1 µm or larger, preferably 5 µm or larger, more preferably 8 µm or larger, while usually 50 µm or smaller, preferably 40 µm or smaller, more preferably 30 µm or smaller. If the separator is significantly thinner than the above range, the insulation and mechanical strength may be poor. If the separator is significantly thicker than the above range, not only the battery performance, such as rate characteristics, may be poor but also the energy density of the whole electrolyte battery may be low.

If the separator is a porous one such as a porous sheet or a nonwoven fabric, the separator may have any porosity. The porosity is usually 20% or higher, preferably 35% or higher, more preferably 45% or higher, while usually 90% or lower, preferably 85% or lower, more preferably 75% or lower. If the porosity is significantly lower than this range, the film resistance tends to be high and the rate characteristics tend to be poor. If the porosity is significantly higher than this range, the mechanical strength of the separator tends to be low and the insulation tends to be poor.

The separator may also have any average pore size. The average pore size is usually 0.5 µm or smaller, preferably 0.2 µm or smaller, whereas the average pore size is usually 0.05 µm or larger. If the average pore size exceeds this range, short circuits may easily occur. If the average pore size is lower than this range, the film resistance may be high and the rate characteristics may be poor.

Examples of the inorganic material include oxides such as alumina and silicon dioxide, nitrides such as aluminum nitride and silicon nitride, and sulfates such as barium sulfate and calcium sulfate, each of which is in the form of particles or fibers.

The separator is in the form of a thin film such as a nonwoven fabric, a woven fabric, or a microporous film. The thin film favorably has a pore size of 0.01 to 1 µm and a thickness of 5 to 50 µm. In addition to the form of the above separate thin film, the separator may have a structure in which a composite porous layer containing particles of the above inorganic material is formed on the surface of one or both of the positive and negative electrodes using a resin binder. For example, alumina particles having a 90% particle size of smaller than 1 µm are applied to the respective surfaces of the positive electrode with fluororesin used as a binder to form a porous layer.

<Battery Design>

The electrode group may be either a laminated structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group proportion) is usually 40% or higher, preferably 50% or higher, while usually 90% or lower, preferably 80% or lower.

If the electrode group proportion is lower than the above range, the battery capacity may be low. If the electrode group proportion exceeds the above range, the battery may have small space for voids. Thus, when the battery temperature rises to high temperature, the components may expand or the liquid fraction of the electrolyte solution shows a high vapor pressure, so that the internal pressure rises. As a result, the battery characteristics such as charge and discharge repeatability and the high-temperature storageability may be impaired, and a gas-releasing valve for releasing the internal pressure toward the outside may work.

The current-collecting structure may be any structure. In order to more effectively improve the high-current-density charge and discharge characteristics by the electrolyte solution, the current-collecting structure is preferably a structure which reduces the resistances at wiring portions and jointing portions. When the internal resistance is reduced in such a manner, the effects of using the electrolyte solution can particularly favorably be achieved.

In an electrode group having the above layered structure, the metal core portions of the respective electrode layers are preferably bundled and welded to a terminal. If one electrode has a large area, the internal resistance is high. Thus, multiple terminals may preferably be formed in the electrode to reduce the resistance. In an electrode group having the wound structure, multiple lead structures may be disposed on each of the positive electrode and the negative electrode and bundled to a terminal. Thereby, the internal resistance can be reduced.

The external case may be made of any material that is stable to an electrolyte solution to be used. Specific examples thereof include metals such as nickel-plated steel plates, stainless steel, aluminum and aluminum alloys, and magnesium alloys, and layered film (laminate film) of resin and aluminum foil. In order to reduce the weight, a metal such as aluminum or an aluminum alloy or a laminate film is favorably used.

External cases made of metal may have a sealed-up structure formed by welding the metal by laser welding, resistance welding, or ultrasonic welding or a caulking structure using the metal via a resin gasket. External cases made of a laminate film may have a sealed-up structure formed by hot-melting the resin layers. In order to improve the sealability, a resin which is different from the resin of the laminate film may be disposed between the resin layers. Especially, in the case of forming a sealed-up structure by hot-melting the resin layers via current-collecting terminals, metal and resin are to be bonded. Thus, the resin to be disposed between the resin layers is favorably a resin having a polar group or a modified resin having a polar group introduced thereinto.

The lithium ion secondary battery may have any shape, and examples thereof include cylindrical batteries, square batteries, laminated batteries, coin batteries, and large-size batteries. The shapes and the configurations of the positive electrode, the negative electrode, and the separator may be changed in accordance with the shape of the battery.

The electrochemical device or secondary battery that includes the above electrolyte solution can be suitably used for a module. This module preferably includes an electrochemical device or secondary battery including the above electrolyte solution.

Examples of the electrochemical device using the electrolyte solution include an electric double-layer capacitor.

In the electric double-layer capacitor, one or both of the positive electrode and the negative electrode is/are a polarizable electrode. The polarizable electrode and a non-polarizable electrode may be the following electrodes specifically disclosed in JP H09-7896 A.

The polarizable electrode mainly containing activated carbon is preferably one containing inactive carbon having a large specific surface area and a conducting agent (e.g., carbon black) which imparts electronic conductivity. The polarizable electrode can be formed by various methods. For example, a polarizable electrode containing activated carbon and carbon black can be formed by mixing activated carbon powder, carbon black, and a phenolic resin, press-molding the mixture, and then firing and activating the mixture in an inert gas atmosphere and in a steam atmosphere. This polarizable electrode is preferably bonded to a current collector using, for example, a conductive adhesive.

Alternatively, a polarizable electrode may be formed by kneading activated carbon powder, carbon black, and a binder in the presence of an alcohol to form a sheet-like mixture, and then drying the sheet-like mixture. This binder may be polytetrafluoroethylene, for example. Alternatively, a polarizable electrode integrated with a current collector may be formed by mixing activated carbon powder, carbon black, a binder, and a solvent to form slurry, applying this slurry to a metal foil of a current collector, and drying the applied slurry.

Both electrodes of the electric double-layer capacitor may be polarizable electrodes mainly containing activated carbon. Alternatively, the electric double-layer capacitor may have a structure in which one electrode thereof is a non-polarizable electrode. Examples of such a structure include a combination of a positive electrode mainly containing a cell active material such as a metal oxide and a negative electrode which is a polarizable electrode mainly containing activated carbon; and a combination of a negative electrode mainly containing a carbon material that can reversibly occlude and release lithium ions or a negative electrode of metallic lithium or a lithium alloy and a polarizable electrode mainly containing activated carbon.

In place of or in combination with activated carbon, a carbonaceous material may be used such as carbon black, graphite, expanded graphite, porous carbon, carbon nanotube, carbon nanohorn, and ketjen black.

The non-polarizable electrode is preferably an electrode mainly containing a carbon material that can reversibly occlude and release lithium ions, and this carbon material is made to occlude lithium ions in advance. In this case, the electrolyte used is a lithium salt. The electric double-layer capacitor having such a configuration achieves a much higher withstand voltage of exceeding 4 V.

The solvent to be used for preparation of slurry in the production of an electrode is preferably one that dissolves a binder. The solvent is appropriately selected from N-methylpyrrolidone, dimethylformamide, toluene, xylene, isophorone, methyl ethyl ketone, ethyl acetate, methyl acetate, dimethyl phthalate, ethanol, methanol, butanol, and water in accordance with the type of the binder.

Examples of the activated carbon to be used for a polarizable electrode include phenol resin-based activated carbon, coconut shell-based activated carbon, and petroleum coke-based activated carbon. In order to achieve a large capacity, petroleum coke-based activated carbon or phenol resin-based activated carbon is preferred. Further, examples of an activation method to prepare activated carbon include steam activation and molten KOH activation. In order to achieve a larger capacity, the use of activated carbon obtainable by the molten KOH activation is preferred.

Preferred examples of the conducting agent to be used for a polarizable electrode include carbon black, ketjen black, acetylene black, natural graphite, artificial graphite, metal fibers, conductive titanium oxide, and ruthenium oxide. In order to achieve good conductivity (low internal resistance), and since too large an amount of the conducting agent may lower the capacity of a product, the amount of the conducting agent (e.g., carbon black) to be used for a polarizable electrode is preferably 1 to 50 mass % in the sum of the amounts of the conducting agent and the activated carbon.

In order to provide an electric double-layer capacitor having a large capacity and a low internal resistance, the activated carbon to be used for a polarizable electrode is preferably activated carbon having an average particle size of 20 μm or smaller and a specific surface area of 1500 to 3000 $m^2$/g. Preferred examples of the carbon material for providing an electrode mainly containing a carbon material that can reversibly occlude and release lithium ions include natural graphite, artificial graphite, graphitized mesocarbon microsphere, graphitized whisker, vapor-grown carbon fiber, sintered furfuryl alcohol resin, and sintered novolak resin.

The current collector may be any one which is chemically and electrochemically resistant to corrosion. Preferred examples of the current collector of a polarizable electrode mainly containing activated carbon include stainless steel, aluminum, titanium, and tantalum. Stainless steel or aluminum is a particularly preferred material among these in terms of both the characteristics and cost of the resulting electric double-layer capacitor. Preferred examples of the current collector to be used for the electrode mainly containing a carbon material that can reversibly occlude and release lithium ions include stainless steel, copper, and nickel.

Examples of methods of allowing the carbon material that can reversibly occlude and release lithium ions to occlude lithium ions in advance include (1) a method of mixing powdery lithium in advance to a carbon material that can reversibly occlude and release lithium ions, (2) a method of placing lithium foil on an electrode including a carbon material that can reversibly occlude and release lithium ions and a binder so that the lithium foil is electrically in contact with the electrode, immersing this electrode in an electrolyte solution containing a lithium salt dissolved therein so that the lithium is ionized, and allowing the carbon material to take in the resulting lithium ions, and (3) a method of placing an electrode including a carbon material that can reversibly occlude and release lithium ions and a binder at a minus side and placing a lithium metal at a plus side, immersing the electrodes in a non-aqueous electrolyte solution containing a lithium salt as an electrolyte, and supplying a current so that the carbon material is allowed to electrochemically take in the ionized lithium.

Examples of commonly known electric double-layer capacitors include wound-type electric double-layer capacitors, laminate-type electric double-layer capacitors, and coin-type electric double-layer capacitors. The electric double-layer capacitor may be of any of these types.

For example, a wound-type electric double-layer capacitor may be assembled by winding a positive electrode and a negative electrode each having a laminate (electrode) of a current collector and an electrode layer with a separator in between to form a wound element, putting this wound element into a case made of, for example, aluminum, filling the case with an electrolyte solution, preferably a non-aqueous electrolyte solution, and then sealing the case with a rubber sealing material.

In the present invention, the separator may be formed from any conventionally known material and may have a conventionally known structure. Examples thereof include a polyethylene porous membrane, and nonwoven fabric of polypropylene fibers, glass fibers, or cellulose fibers.

Alternatively, by a known method, an electric double-layer capacitor may be prepared in the form of a laminate-type electric double layer capacitor including a sheet-like positive and negative electrodes stacked with each other with an electrolyte solution and a separator in between, or in the form of a coin-type electric double-layer capacitor including a positive electrode and a negative electrode fixed in a coin shape using a gasket with an electrolyte solution and a separator in between.

As mentioned above, use of the electrolyte solution can suitably provide secondary batteries having excellent storage capacity retention, modules using the secondary batteries, and electric double-layer capacitors.

EXAMPLES

The present invention will be described with reference to, but not limited to, examples.

Synthesis Example 1

Bromovinylene carbonate represented by the following formula was synthesized according to the method disclosed in Chem. Ber. 103, 1970, 3949.

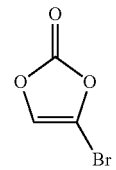

A 500-mL glass reactor was charged with 7.93 g of zinc, 3.50 g of tetrakistriphenylphosphinepalladium, 10.00 g of bromovinylene carbonate, and 150.00 ml of cyclopentyl methyl ether. Then, 52.43 g of perfluorobutyl iodide was dropwise added under ultrasonic irradiation, and the components were stirred for 6 hours at room temperature.

After the reaction aged, 150.00 g of a saturated aqueous solution of sodium chloride was added so that the reaction was quenched. The reaction solution was extracted with diisopropyl ether, and then magnesium sulfate was added so that the extract was dried. Then, the dried product was concentrated and purified by sublimation. Thereby, 1.16 g of 4-perfluorobutyl-vinylene carbonate ($C_4F_9VC$), the target compound, was obtained as a white solid.

The analysis showed that 4-perfluorobutyl-vinylene carbonate represented by the following formula was obtained.

$^1$H-NMR (acetone-d6): δ8.45 (t, J=2.39 Hz, 1H)

$^{13}$C-NMR (acetone-d6): δ110.13 to 111.05 (m), 112.49 to 114.03 (m), 116.52 (t, J=133.90 Hz), 119.38 (t, J=133.90 Hz), 132.18 (t, J=139.89 Hz), 136.02 (t, J=23.98 Hz), 151.23

$^{19}$F-NMR (acetone-d6): δ−79.43 (t, J=10.53 Hz, 3F), −113.39 (t, J=12.03 Hz, 2F), −121.56 (dd, J=8.56, 2.26 Hz, 2F), −124.18 to −124.26 (m, 2F)

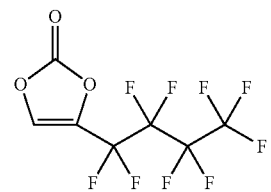 [SMILES: O=c1occ(C(F)(F)C(F)(F)C(F)(F)C(F)(F)F)o1]

Synthesis Example 2

Bromovinylene carbonate represented by the following formula was synthesized according to the method disclosed in Chem. Ber. 103, 1970, 3949.

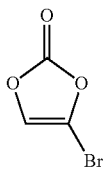

A 500-mL glass reactor was charged with 15.44 g of copper, 50.85 g of $(C_6F_{13})_2Hg$, and 90.00 ml of dimethylacetamide, and the components were stirred for 2 hours at 140° C. Then, 10.00 g of bromovinylene carbonate dissolved in 90.00 ml of dimethylacetamide was dropwise added and the components were stirred for 6 hours at 140° C.

After the reaction aged, 100.00 g of a saturated aqueous solution of sodium chloride was added so that the reaction was quenched. The reaction solution was extracted with ethyl acetate, and then magnesium sulfate was added so that the extract was dried. Then, the dried product was concentrated and purified by sublimation. Thereby, 4.73 g of 4-perfluorohexyl-vinylene carbonate ($C_6F_{13}VC$), the target compound, was obtained as a white solid.

The analysis showed that 4-perfluorohexyl-vinylene carbonate represented by the following formula was obtained.

$^1$H-NMR (acetone-d6): δ8.47 (t, J=2.39 Hz, 1H)

$^{13}$C-NMR (acetone-d6): δ105.97 to 107.27 (m), 108.52 to 109.83 (m), 111.06 to 112.20 (m), 114.32 (t, J=130.69 Hz), 117.18 (t, J=130.69 Hz), 120.05 (t, J=137.09 Hz), 129.91 (t, J=136.69 Hz), 134.29 (t, J=25.18 Hz), 149.24

$^{19}$F-NMR (acetone-d6): δ−81.71 (t, J=9.02 Hz, 3F), −115.71 (t, J=12.03 Hz, 2F), −122.47 (s, 2F), −123.17 (d, J=6.76 Hz, 2F), −123.42 (d, J=7.14 Hz, 2F), −126.76 to −126.85 (m, 2F)

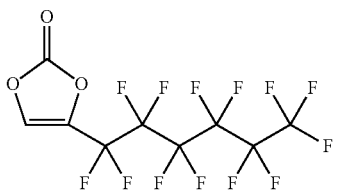 [SMILES: O=c1occ(C(F)(F)C(F)(F)C(F)(F)C(F)(F)C(F)(F)C(F)(F)F)o1]

Synthesis Example 3

Bromovinylene carbonate represented by the following formula was synthesized according to the method disclosed in Chem. Ber. 103, 1970, 3949.

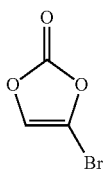

A 500-mL glass reactor was charged with 1.15 g of copper iodide, 200.00 ml of dimethylpropyleneurea, 7.04 g of potassium fluoride, 35.43 g of $C_4F_9TMS$, and 1.09 g of 1,10-phenanthroline. Then, 10.00 g of bromovinylene carbonate was dropwise added, and the components were stirred for 20 hours at 80° C.

After the reaction aged, 100.00 g of a saturated aqueous solution of sodium chloride was added so that the reaction was quenched. The reaction solution was extracted with ethyl acetate, and then magnesium sulfate was added so that the extract was dried. Then, the dried product was concentrated and purified by sublimation. Thereby, 9.07 g of 4-perfluorobutyl-vinylene carbonate ($C_4F_9VC$), the target compound, was obtained as a white solid.

The analysis showed that 4-perfluorobutyl-vinylene carbonate represented by the following formula was obtained.

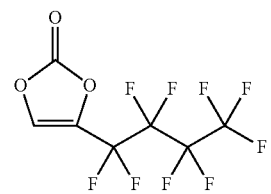 [SMILES: O=c1occ(C(F)(F)C(F)(F)C(F)(F)C(F)(F)F)o1]

Synthesis Example 4

A 1000-mL photo-reactor was equipped with a 100-W high-pressure mercury lamp, and charged with 20.00 g of 4-perfluorohexyl-ethylene carbonate represented by the following formula and 197.00 mL of carbon tetrachloride.

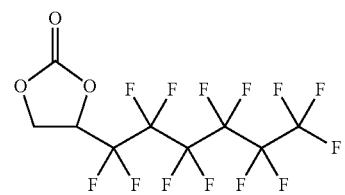 [SMILES: O=C1OCC(C(F)(F)C(F)(F)C(F)(F)C(F)(F)C(F)(F)C(F)(F)F)O1]

Under light irradiation from the high-pressure mercury lamp, 9.44 g of bromine dissolved in 98.49 mL of carbon tetrachloride was dropwise added. This dropwise addition was followed by stirring for 2 hours at room temperature. After the reaction aged, 186.22 g of a 10% aqueous solution of sodium sulfite was added so that the reaction was quenched. Then, an organic layer obtained by liquid separation was used in the next step as a reaction solution. The reaction solution contains a carbonate represented by the following formula.

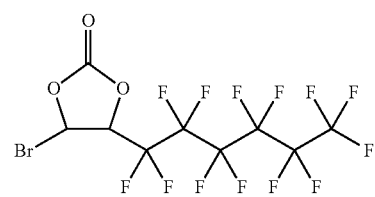 [SMILES: O=C1OC(Br)C(C(F)(F)C(F)(F)C(F)(F)C(F)(F)C(F)(F)C(F)(F)F)O1]

The reaction solution obtained in the above procedure was put into a 1000-mL glass reactor, and 5.98 g of triethylamine was dropwise added under ice cooling. This dropwise addition was followed by stirring for 3 hours. After the reaction aged, 113.54 g of a 10% aqueous solution of citric acid was added so that the reaction was quenched. Then, magnesium sulfate was added to an organic layer obtained by liquid separation so that the organic layer was dried. The magnesium sulfate was filtered out and the filtrate was concentrated. Thereby, crude 4-perfluorohexyl-carbonate was obtained.

The crude product was then purified by sublimation. Thereby, 4.36 g of 4-perfluorohexyl-vinylene carbonate ($C_6F_{13}VC$), the target compound, was obtained as a white solid.

The analysis showed that 4-perfluorohexyl-vinylene carbonate represented by the following formula was obtained.

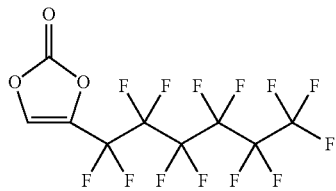 [SMILES: O=c1occ(C(F)(F)C(F)(F)C(F)(F)C(F)(F)C(F)(F)C(F)(F)F)o1]

Synthesis Example 5

A 1000-mL photo-reactor was equipped with a 100-W high-pressure mercury lamp, and charged with 20.00 g of 4-perfluorobutyl-ethylene carbonate represented by the following formula and 261.37 mL of carbon tetrachloride.

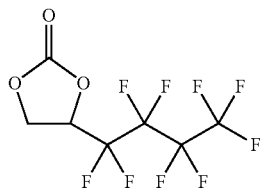 [SMILES: O=C1OCC(C(F)(F)C(F)(F)C(F)(F)C(F)(F)F)O1]

Under light irradiation from the high-pressure mercury lamp, 12.53 g of bromine dissolved in 130.68 mL of carbon tetrachloride was dropwise added. This dropwise addition was followed by stirring for 2 hours at room temperature. After the reaction aged, 247.07 g of a 10% aqueous solution of sodium sulfite was added so that the reaction was quenched. Then, an organic layer obtained by liquid separation was used in the next step as a reaction solution. The reaction solution contains a carbonate represented by the following formula.

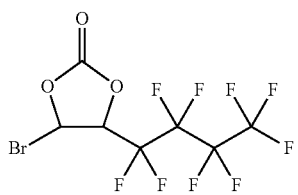 [SMILES: O=C1OC(Br)C(C(F)(F)C(F)(F)C(F)(F)C(F)(F)F)O1]

The reaction solution obtained in the above procedure was put into a 1000-mL glass reactor, and 7.93 g of triethylamine was dropwise added under ice cooling. This dropwise addition was followed by stirring for 3 hours. After the reaction aged, 150.64 g of a 10% aqueous solution of citric acid was added so that the reaction was quenched. Then, magnesium sulfate was added to an organic layer obtained by liquid separation so that the organic layer was dried. The magnesium sulfate was filtered out and the filtrate was concentrated. Thereby, crude 4-perfluorobutyl-vinylene carbonate was obtained.

The crude product was then purified by sublimation. Thereby, 5.05 g of 4-perfluorobutyl-vinylene carbonate, the target compound, was obtained as a white solid.

The analysis showed that 4-perfluorobutyl-vinylene carbonate represented by the following formula was obtained.

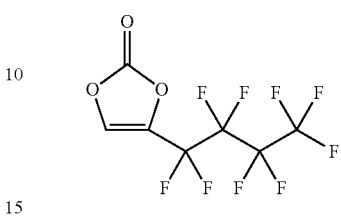

Synthesis Example 6

A 200-mL glass reactor was equipped with a condenser, and charged with 2.15 g of LiBr and 40.00 mL of N-methylpyrrolidone (NMP). Then, the components were stirred for 1 hour at 35° C. The atmosphere inside the reactor was replaced by carbon dioxide, and 10.00 g of an epoxy represented by the following formula was dropwise added. This dropwise addition was followed by stirring for 6 hours at 35° C.

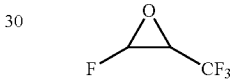

After the reaction aged, 20 mL of a saturated aqueous solution of sodium chloride was added so that the reaction was quenched. The reaction solution was extracted with ethyl acetate, and then magnesium sulfate was added so that the extract was dried. Then, the dried product was concentrated. Thereby, a carbonate represented by the following formula was obtained.

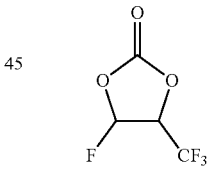

The carbonate obtained in the above procedure and 53.60 mL of diethyl ether were put into a 300-mL glass reactor, and 6.51 g of triethylamine was dropwise added under ice cooling. This dropwise addition was followed by stirring for 3 hours. After the reaction aged, 123.58 g of a 10% aqueous solution of citric acid was added so that the reaction was quenched. Then, magnesium sulfate was added to an organic layer obtained by liquid separation so that the organic layer was dried. The magnesium sulfate was filtered out and the filtrate was concentrated. Thereby, crude 4-trifluoromethyl-vinylene carbonate was obtained.

The crude product was then purified by distillation. Thereby, 3.77 g of 4-trifluoromethyl-vinylene carbonate ($CF_3VC$), the target compound, was obtained as a colorless liquid.

The analysis showed that 4-trifluoromethyl-vinylene carbonate represented by the following formula was obtained.

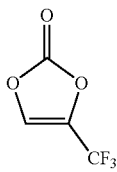

Synthesis Example 7

A 300-mL autoclave was charged with 10.00 g of vinylene carbonate, 103.65 g of perfluorohexyl iodide, and 1.02 g of t-butylperoxyisopropylmonocarbonate, and the components were stirred for 6 hours at 120° C. After the reaction aged, the reaction solution was concentrated. Thereby, crude $C_6F_{13}ECI$ was obtained as a white solid. $C_6F_{13}ECI$ is a carbonate represented by the following formula.

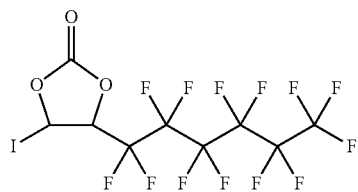 [SMILES: O=C1OC(I)C(C(F)(F)C(F)(F)C(F)(F)C(F)(F)C(F)(F)C(F)(F)F)O1]

Next, 61.45 g of the crude $C_6F_{13}ECI$ and 231.02 mL of diethyl ether were put into a 500-mL glass reactor. Then, 14.03 g of triethylamine was dropwise added under ice cooling. This dropwise addition was followed by stirring for 3 hours. After the reaction aged, 159.78 g of a 20% aqueous solution of citric acid was added so that the reaction was quenched. The reaction solution was extracted with diethyl ether, and then magnesium sulfate was added so that the extract was dried. Then, the dried product was concentrated and purified by sublimation. Thereby, 31.02 g of 4-perfluorohexyl-vinylene carbonate ($C_6F_{13}VC$), the target compound, was obtained as a white solid.

The analysis showed that 4-perfluorohexyl-vinylene carbonate represented by the following formula was obtained.

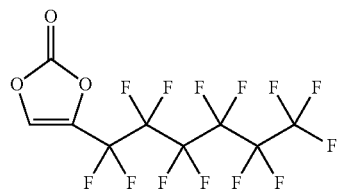 [SMILES: O=c1occ(C(F)(F)C(F)(F)C(F)(F)C(F)(F)C(F)(F)C(F)(F)F)o1]

Synthesis Example 8

A 300-mL autoclave was charged with 10.00 g of vinylene carbonate, 80.40 g of perfluorobutyl iodide, and 1.02 g of t-butylperoxyisopropylmonocarbonate, and the components were stirred for 6 hours at 120° C. After the reaction aged, the reaction solution was concentrated. Thereby, crude $C_4F_9ECI$ was obtained as a white solid. $C_4F_9ECI$ is a carbonate represented by the following formula.

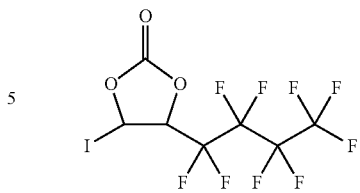

Next, 49.50 g of the crude $C_4F_9ECI$ and 229.18 mL of diethyl ether were put into a 500-mL glass reactor. Then, 13.91 g of triethylamine was dropwise added under ice cooling. This dropwise addition was followed by stirring for 3 hours. After the reaction aged, 158.51 g of a 20% aqueous solution of citric acid was added so that the reaction was quenched. The reaction solution was extracted with diethyl ether, and then magnesium sulfate was added so that the extract was dried. Then, the dried product was concentrated and purified by sublimation. Thereby, 24.42 g of 4-perfluorobutyl-vinylene carbonate ($C_4F_9VC$), the target compound, was obtained as a white solid.

The analysis showed that 4-perfluorobutyl-vinylene carbonate represented by the following formula was obtained.

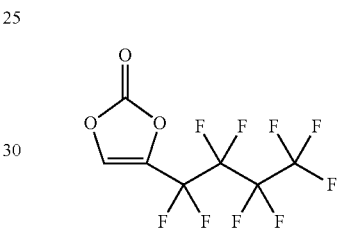

Experiment 1 (Evaluation of 4.2-V Lithium Battery)

Example 1

In dry argon atmosphere, 0.5 parts by weight of 4-perfluorohexyl-vinylene carbonate obtained in Synthesis Example 4 and 0.5 parts by weight of vinylene carbonate (VC) were added to 99 parts by weight of a mixture of ethylene carbonate and ethyl methyl carbonate (volume ratio=3:7). Then, sufficiently dried $LiPF_6$ was dissolved therein so as to have a concentration of 1 mol/L. Thereby, an electrolyte solution was prepared.

(Production of Laminate Battery)

$LiNi_{1/3}Mn_{1/3}Co_{1/3}O_2$, carbon black, and polyvinylidene fluoride (trade name: KF-7200, Kureha Chemical Industry Co., Ltd.) were mixed at a ratio of 92/3/5 (mass % ratio) to provide a positive electrode active material. This positive electrode active material was dispersed in N-methyl-2-pyrrolidone to form a positive electrode mixture slurry. The resulting positive electrode mixture slurry was uniformly applied onto an aluminum current collector and dried to provide a positive electrode mixture layer (thickness: 50 μm). Then, the workpiece was compression-molded using a roller press. Thereby, a positive electrode laminate was produced.

Separately, styrene-butadiene rubber dispersed in distilled water was added to artificial graphite powder such that the solid content of the rubber was 6 mass %, and the components were mixed using a disperser to form a slurry-like mixture. This mixture was uniformly applied onto a negative electrode current collector (10-μm-thick copper foil) and dried. Thereby, a negative electrode mixture layer was formed. Then, the workpiece was compression-molded using a roller press. Thereby, a negative electrode laminate was produced.

The positive electrode laminate and the negative electrode laminate were oppositely disposed with a 20-μm-thick microporous polyethylene film (separator) interposed in between, and wound to provide a wound article. This wound article was placed in an aluminum-laminated film and an electrolyte solution was put thereinto. After the electrolyte solution sufficiently permeated into the separator and other desired components, the package was sealed, pre-charged, and aged. Thereby, a 1-Ah lithium ion secondary battery was produced.

(Measurement of Battery Performance)

For a coin-type lithium secondary battery, the cycle characteristics and the high-temperature storage characteristics at high voltage were analyzed as follows.

Charge and Discharge Conditions

Charge: 1 C, 4.2 V, retained until the charge current reaches 1/10 C (CC/CV charge)

Discharge: 1 C, 3.0 V cut (CC discharge)

(High-Temperature Storage Characteristics)

For the high-temperature storage characteristics, the battery was charged and discharged according to the above charge and discharge conditions (charged at 1.0 C and a predetermined voltage until the charge current reached 1/10 C, and discharged at a current corresponding to 1 C until the voltage reached 3.0 V), whereby the discharge capacity was examined. Then, the battery was again charged according to the above charge conditions, and then stored in a 85° C. temperature-constant chamber for 3 days. The battery after the storage was placed in a 25° C. atmosphere, and was discharged according to the above discharge conditions until the end-of-discharge voltage, 3 V, and the residual capacity was measured. The battery was further charged according to the above charge conditions and discharged according to the above discharge conditions at a constant current until the end-of-discharge voltage, 3 V, and the capacity recovery was measured. Table 1 shows the capacity recovery relative to the discharge capacity before storage which is defined as 100.

Table 1 also shows the amount (mL) of gas generated in this case.

Example 2

A battery was produced and the experiment was performed in the same manner as in Example 1 except that 4-perfluorohexyl-vinylene carbonate prepared in Synthesis Example 4 was replaced by 4-perfluorobutyl-vinylene carbonate prepared in Synthesis Example 5. Table 1 shows the results.

Example 3

A battery was produced and the experiment was performed in the same manner as in Example 1 except that 4-perfluorohexyl-vinylene carbonate prepared in Synthesis Example 4 was replaced by 4-trifluoromethyl-vinylene carbonate prepared in Synthesis Example 6. Table 1 shows the results.

Comparative Example 1

A battery was produced and the experiment was performed in the same manner as in Example 1 except that the amount of VC was increased by 0.5 wt % (i.e., 1.0 part by weight of VC was added in total) instead of adding 4-perfluorohexyl-vinylene carbonate. Table 1 shows the results.

TABLE 1

| | High-temperature storage characteristics | |
|---|---|---|
| | Capacity recovery | Amount of gas |
| Example 1 | 92.1 | 0.73 |
| Example 2 | 93.2 | 0.60 |
| Example 3 | 93.9 | 0.55 |
| Comparative Example 1 | 85.2 | 0.97 |

Comparison between Examples 1 to 3 and Comparative Example 1 in Table 1 shows that the presence of the compound (1) led to less generation of gas and higher capacity recovery than the use of VC alone.

What is claimed is:

1. An electrolyte solution comprising a compound represented by the following formula (1):

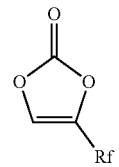

wherein Rf is a C1-C8 fluorinated alkyl group, and vinylene carbonate.

2. An electrochemical device comprising the electrolyte solution according to claim 1.

3. A lithium ion secondary battery comprising the electrolyte solution according to claim 1.

4. A module comprising the lithium ion secondary battery according to claim 3.

* * * * *